US005418153A

United States Patent [19]

Mori et al.

[11] Patent Number: 5,418,153

[45] Date of Patent: May 23, 1995

[54] PROCESS FOR PRODUCTION OF EXOGENOUS GENE OR ITS PRODUCT IN PLANT CELLS

[75] Inventors: Masashi Mori; Tetsuro Okuno; Iwao Furusawa, all of Kyoto, Japan

[73] Assignee: Nihon Nohyaku Co., Ltd., Tokyo, Japan

[21] Appl. No.: 53,564

[22] Filed: Apr. 28, 1993

[30] Foreign Application Priority Data

Apr. 28, 1992 [JP] Japan .................................. 4-152593

[51] Int. Cl.[6] ........................ C12N 15/00; C12N 7/00; C12P 21/04; C07H 21/04

[52] U.S. Cl. ................................ 435/172.3; 435/69.1; 435/70.1; 435/235.1; 435/320.1; 536/23.2; 536/23.72

[58] Field of Search .................... 435/69.1, 69.51, 70.1, 435/172.3, 240.4, 320.1, 235.1; 800/205, DIG. 15, 18, 23, 40, 43, 45, 55; 536/23.2, 23.52, 23.72

[56] References Cited

U.S. PATENT DOCUMENTS 4,956,282 9/1990 Goodman et al. ............... 435/69.51

FOREIGN PATENT DOCUMENTS 636717 3/1992 Australia ....................... C12N 15/33
0278667 8/1988 European Pat. Off. ...... C12N 15/00
4121200 4/1992 Japan ............................ C12N 15/00

OTHER PUBLICATIONS

Ahlquist et al. 1984. Mol. Cell. Biol. 4(12): 2876–2882.
Mori et al. 1992. J. Gen. Virol. 73(1): 169–172.
Mise et al. 1992. J. Gen. Virol. 73(10): 2543–2551.
Tacke et al. 1990. J. Gen. Virol. 71:2265–2272.
Sacher et al. 1989. J. Virol. 63(11): 4545–4552.
French et al. 1986. Science 231: 1294–1297.
Ishikawa et al. 1991. J. Virol. 65(7): 3451–3459.
Haseloff et al. 1984. Proc. Natl. Acad. Sci. USA 81: 4358–4362.
Van Dun et al. 1988. Virology 163: 572–578.
Journal Of General Virology, vol. 73, 1992, pp. 169–172, M. Mori et al, "Expression of brome mosaic virus-encoded replicase genes in transgenic tobacco plants".
Science, vol. 231, 1986, R. French et al, "Bacterial Gene Inserted in an Engineered RNA Virus; Efficient Expression in Monocotyledonous Plant Cells", pp. 1294–1297.
The EMBO Journal, vol. 6, 1987, N. Takamatsu et al, "Expression of bacterial acetyltransferase gene in tobacco plants mediated by TMV-RNA", pp. 307-311
Annual Review Of Phytopathology, vol. 28, 1990, pp. 451–474, R. N. Beachy et al, "Coat Protein-Mediated Resistance Against Virus Infection".

*Primary Examiner*—David T. Fox
*Attorney, Agent, or Firm*—Sughrue, Mion, Zinn, Macpeak & Seas

[57] ABSTRACT

A process for production of an exogenous gene or its product in a plant cell which comprises:

inserting into a genome of a plant;

a) cDNA of replicase gene from RNA plant virus, and b) cDNA of a recombinant virus genomic RNA in which nucleotide moiety at and after ATG downstream from the original translation initiation codon (the first ATG counted from the 5'-end) in the cDNA of coat protein gene is replaced with a desired exogenous gene; or inoculating a plant cell including cDNA of replicase gene of a plant virus with synthesized RNA synthesized from the cDNA of recombinant virus genomic RNA.

2 Claims, 18 Drawing Sheets

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 34 base pairs
( B ) TYPE: nucleic acid
( C ) STRANDEDNESS: double
( D ) TOPOLOGY: linear ( i i ) MOLECULE TYPE: cDNA of genomic RNA ( x i ) SEQUENCE DESCRIPTION: SEQ ID NO:1:

GTATTTAATG TCGACTTCAG GAACTGGTAA GATG 34

( 2 ) INFORMATION FOR SEQ ID NO:2:

( i ) SEQUENCE CHARACTERISTICS:
( A ) LENGTH: 31 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:2:

CTAGATGCAT ATAGTGAGTC GTATTAATTT A 31

( 2 ) INFORMATION FOR SEQ ID NO:3:

( i ) SEQUENCE CHARACTERISTICS:
( A ) LENGTH: 31 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide -continued ( x i ) SEQUENCE DESCRIPTION: SEQ ID NO:3:

AGCTTAAATT AATACGACTC ACTATATGCA T 31

( 2 ) INFORMATION FOR SEQ ID NO:4:

( i ) SEQUENCE CHARACTERISTICS:
( A ) LENGTH: 25 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:4:

GTAGGCCTCT CCAAATGAAA TGAAC 25

( 2 ) INFORMATION FOR SEQ ID NO:5:

( i ) SEQUENCE CHARACTERISTICS:
( A ) LENGTH: 38 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:5:

GTTTTTCACC AACAAAATGC ATAGTTCTAT CGATTTGC 38

( 2 ) INFORMATION FOR SEQ ID NO:6:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:6:

CACCAAGATG CATTCGAAAA CC 22

( 2 ) INFORMATION FOR SEQ ID NO:7:

( i ) SEQUENCE CHARACTERISTICS:
( A ) LENGTH: 23 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:7:

GTTCCCGATG CATAACATAG TTT 23

( 2 ) INFORMATION FOR SEQ ID NO:8:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:8:

-continued

GTATTTAATG CATACTTCAG GAAC 24

( 2 ) INFORMATION FOR SEQ ID NO:9:

( i ) SEQUENCE CHARACTERISTICS:
( A ) LENGTH: 22 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:9:

TGGTAAGATG CACGCGCGCA GC 22

( 2 ) INFORMATION FOR SEQ ID NO:10:

( i ) SEQUENCE CHARACTERISTICS:
( A ) LENGTH: 28 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:10:

TCTCTCGGAA TGCATGCATG AAATATAC 28

( 2 ) INFORMATION FOR SEQ ID NO:11:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:11:

CCCAGTAATG GAGCTCCTGC CTGC 24

( 2 ) INFORMATION FOR SEQ ID NO:12:

( i ) SEQUENCE CHARACTERISTICS:
( A ) LENGTH: 10 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:12:

GTATTTAATG 10

( 2 ) INFORMATION FOR SEQ ID NO:13:

( i ) SEQUENCE CHARACTERISTICS:
( A ) LENGTH: 14 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:13:

TCGACATTAA ATAC 14

-continued ( 2 ) INFORMATION FOR SEQ ID NO:14:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:14:

GTGGTCAGTC ATGCATGTTA CGTA 24

( 2 ) INFORMATION FOR SEQ ID NO:15:

( i ) SEQUENCE CHARACTERISTICS:
( A ) LENGTH: 24 bases
( B ) TYPE: nucleic acid
( C ) STRANDEDNESS: single
( D ) TOPOLOGY: linear ( i i ) MOLECULE TYPE: Other nucleic acid
( A ) DESCRIPTION: synthesized oligonucleotide ( x i ) SEQUENCE DESCRIPTION: SEQ ID NO:15:

AATGAATCAA GAGCTCTCCT GGCG 24

PROCESS FOR PRODUCTION OF EXOGENOUS GENE OR ITS PRODUCT IN PLANT CELLS

BACKGROUND OF THE INVENTION

1. Field of the Invention

The present invention relates to a process for producing in plant cells substances useful in agricultural and pharmaceutical fields, by producing large quantities of an exogenous gene or its products in plant cells capable of producing replicase of RNA plant virus, e.g., brome mosaic checks virus (hereinafter referred to as BMV), by genetic engineering techniques. Also, the present invention relates to a process for producing useful transformed plants capable of expressing useful characteristics. The present invention further relates to vectors for plant transformation and vectors capable of producing recombinant RNA as well as transformed plant cells.

2. Description of the Related Art

Development of a method for introducing and expressing an exogenous gene in a plant genome using the Ti plasmid transformation system and of a method for utilizing the multiplication system of a plant virus is under way as a technique for producing useful polypeptides in plant cells or as a method for imparting useful characteristics, for example, plant virus resistance, to plants by useful polypeptide. It is known that in the case of introducing a coat protein gene of tobacco mosaic virus (TMV) into a plant genome using the Ti plasmid transformation system, the amount of coat protein produced is at most 0.01% of the total plant protein (Beachy et al., *Annu. Rev. Phytopath.* (1990), 28:451–474).

According to this technique, the amount of the product produced by an exogenous gene is dependent on promoter activity which regulates the amount of transcription so that evaluation of promoters capable of imparting a more potent transcription activity becomes necessary. On the other hand, TMV can produce at the maximum 2 g of virus particles per kg of leaves in a host plant.

In the case of a method of utilizing the multiplication system of a plant virus which comprises replacing the exogenous gene of a desired substance for the gene moiety of TMV coat protein and inoculating a host plant with the resulting recombinant, the amount of the desired substance produced was about 1 mg/kg of leaves (Takamatsu et al., *EMBO J.* (1987), 6:307–311).

Turning to the problem involved in TMV, three kind of genes are overlappingly encoded on one single strand of RNA in TMV. It is thus considered that by replacement of an exogenous gene, the regulating mechanism of TMV replication would be affected. For this reason, use of plant viruses having a virus genome divided on several kinds of single stranded RNAs has been investigated.

As an example, there is a BMV which uses as a host many plants belonging to the family Gramineae and which falls under the bromo virus group. The genome of BMV is composed of three kinds of (+) single stranded RNAs and these RNAs are called RNAs 1, 2 and 3, in terms of decreasingly larger molecular weight. In addition, RNA4 called subgenomic RNA also exists in BMV. These RNAs are enclosed in spherical particles having a diameter of about 26 nm, with RNA1 and 2 being alone, respectively and RNA3 and 4 being together (Lane et al., *Adv. Virus Res.* (1974), 19:151–220).

The advantages of using BMV are 1) the amount of multiplication in a infected plant cell is high, and 2) its regulating mechanism of virus replication is affected with difficulty on replacement of the exogenous gene in a coat protein gene, and hence, only replicase is required for replication, and 3a protein and coat protein are not concerned with the virus replication, because of the characteristics of the divided genomes. The nucleotide sequence of the entire genome of BMV has already been determined (Ahlquist et al., *J. Mol. Biol.* (1984), 172:369–383); RNA1 has 3234 bases full length and encodes 1a protein (molecular weight of 109 kilodaltons (KD)), RNA2 has 2865 bases full length and encodes 2a protein (molecular weight of 94 KD), and 1a and 2a proteins are considered to be replicase subunits.

It is thought that in (+)-stranded BMV RNA, (−)-stranded RNA would be synthesized from (+)-stranded RNA in a plant cell by this replicase and using the synthesized (−)-stranded RNA as a template, (+)-stranded RNA would be synthesized in large quantities. On the other hand, RNA3 has 2134 bases full length and encodes the two genetic products of 3a protein (molecular weight of 34 KD), and coat protein (molecular weight of 20 KD) but only the 3a protein encoded on the 5′ side is directly translated from RNA3. RNA4 has 876 bases full length, possesses the same sequence as that of the coat protein gene portion of RNA3, and becomes mRNA for coat protein. RNA4 is synthesized from RNA3 in a host cell (Ahlquist et al., *J. Mol. Biol.* (1981), 153:23–38).

The mechanism shows that (−)-stranded RNA3 is synthesized from (+)-stranded RNA3 and (+)-stranded RNA4 is synthesized from the inside of this (−)-strand (Miller et al., *Nature* (1985), 313:68–70). Alquist succeeded in expressing chloramphenicol acetyl transferase (CAT) on a high level, by removing most of the coat protein gene from RNA3, introducing CAT gene at the removal site, and infecting bare protoplasts with the resulting recombinant RNA3 together with RNAs 1 and 2. However, they failed to utilize this technique in expression of CAT gene on a plant level (Ahlquist et al., *Science* (1986), 231:1294–1297).

As described above, in constructing a vector from a virus where the virus genome as represented by BMV, cucumber mosaic virus (hereinafter referred to as CMV) alfalfa mosaic virus (hereinafter referred to as AMV) is divided into 4 RNA chains, BMV has been studied most extensively.

In the method wherein the recombinant RNA3 in which the coat protein gene has been replaced with an exogenous gene is merely mixed with RNAs 1 and 2 and a plant protoplast is inoculated with the mixture to produce the exogenous gene in the protoplast, there is the problem that the amount of expression in each cell is small, because the infection efficiency of the protoplast by the RNA is poor and the recombinant virus RNA cannot be systematically infected.

Furthermore, this technique can not be utilized for obtaining a genetically transformed plant. Moreover, industrial production of virus RNA in vitro has serious disadvantages in view of costs. To overcome these problems, the following method has been developed (Mori et al., *J. Gen. Virol.* (1992), 73:169–172, U.S. patent application Ser. No. 07/663,164). That is, the method using a genetic engineering technique which comprises constructing genomic RNAcDNA of RNA plant virus including BMV and recombinant cDNA where the coat protein gene of virus genomic RNAcDNA is replaced with an exogenous gene, modifying them to express the virus RNA in a plant cell, and inserting them into the genome of a plant using a plant cell transformation method, such as Ti plasmid, etc., or by a DNA direct introduction method, such as electroporation, etc. Thus virus replicase is produced in all cells and recombinant RNA containing the exogenous gene is replicated to express mRNA of the exogenous gene in large quantities. In this case, multiplication of virus RNA in large amounts causes the plants to be diseased and adversely affects the growth of plants. Therefore, multiplication of virus RNA other than the exogenous gene is not considered to be necessarily required. So, a method for modifying the virus genome to delete the ability of RNAs 1 and 2 to multiply in the case of genomic RNA containing the virus replicase gene, for example, BMV, and as the result, translation of la and 2a protein (BMV replicase) alone, has been developed simultaneously (Mori et al., *J. Gen. Virol.* (1992), 73:169–172, U.S. patent application Ser. No. 07/663,164).

Further, with BMV as an example, sites of 1a, 2a, 3a and coat protein genes can be considered as replacement sites for exogenous genes, which produce the desired proteins which are not fusion proteins. In case of BMV, depending on the strain, a coat protein of 19 KD (CP2) is known to be also produced in addition to a coat protein of 20 KD (CP1) (Sacher and Ahlquist, *J. Virology* (1989), 63:4545–4552). As a result of extensive studies on the BMV gene to provide a superior method for production, the present inventors have accomplished this invention.

SUMMARY OF THE INVENTION

The present invention provides a method for producing an exogenous gene and its expression product in large quantity and efficiently, the method comprising either inserting cDNA of the replicase gene of a plant virus and the cDNA of recombinant virus genome containing a coat protein gene replaced with an exogenous gene independently, or inoculating a plant cell having cDNA of the replicase gene of a plant virus inserted into the plant genome with synthesized gene from cDNA of a recombinant virus genome.

PKT: NOS promoter, kanamycin-resistant gene and NOS terminator

35: CaMV35S promoter

T: CaMV terminator

▸: T-DNA border sequence of Ti plasmid

▧: cDNA corresponding to non-translated region of BMVRNA

▨: cDNA corresponding to translated region of BMVRNA

Figure 3:
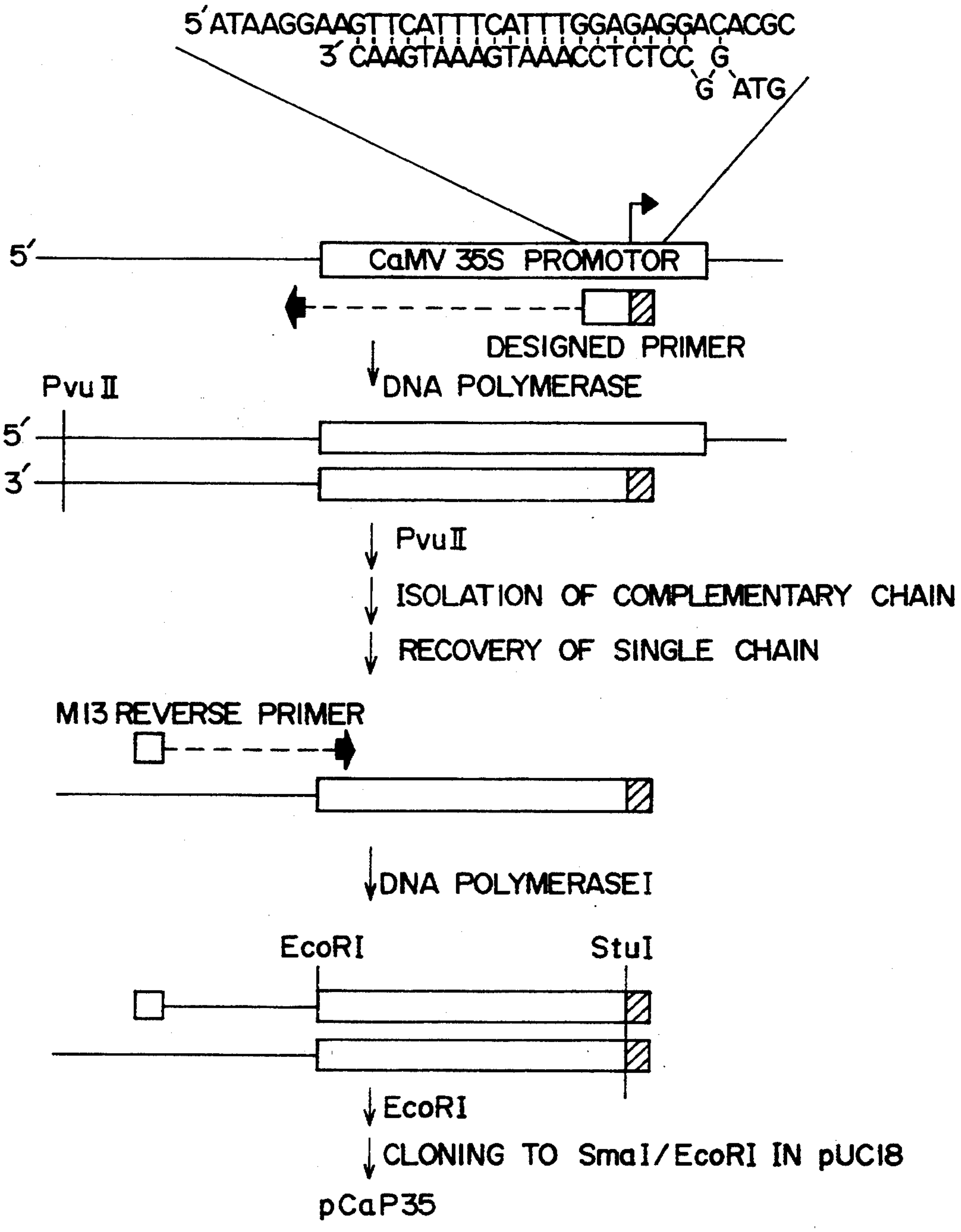

↱: transcription initiation site and transcription direction type (1): vector for transformation in which full length cDNA of BMV RNA was inserted type (2): vector for transformation in which the cDNA of BMVRNA with a deletion of only the nucleotide portion corresponding to 3′ non-translated region was inserted FIG. 3 shows a process for introducing the restriction enzyme site (StuI) into the transcription initiation site of CaMV35S promoter by site-directed mutagenesis.

▨: base sequence introduced mutagenesis

↱: transcription initiation site and transcription direction

Figure 4:
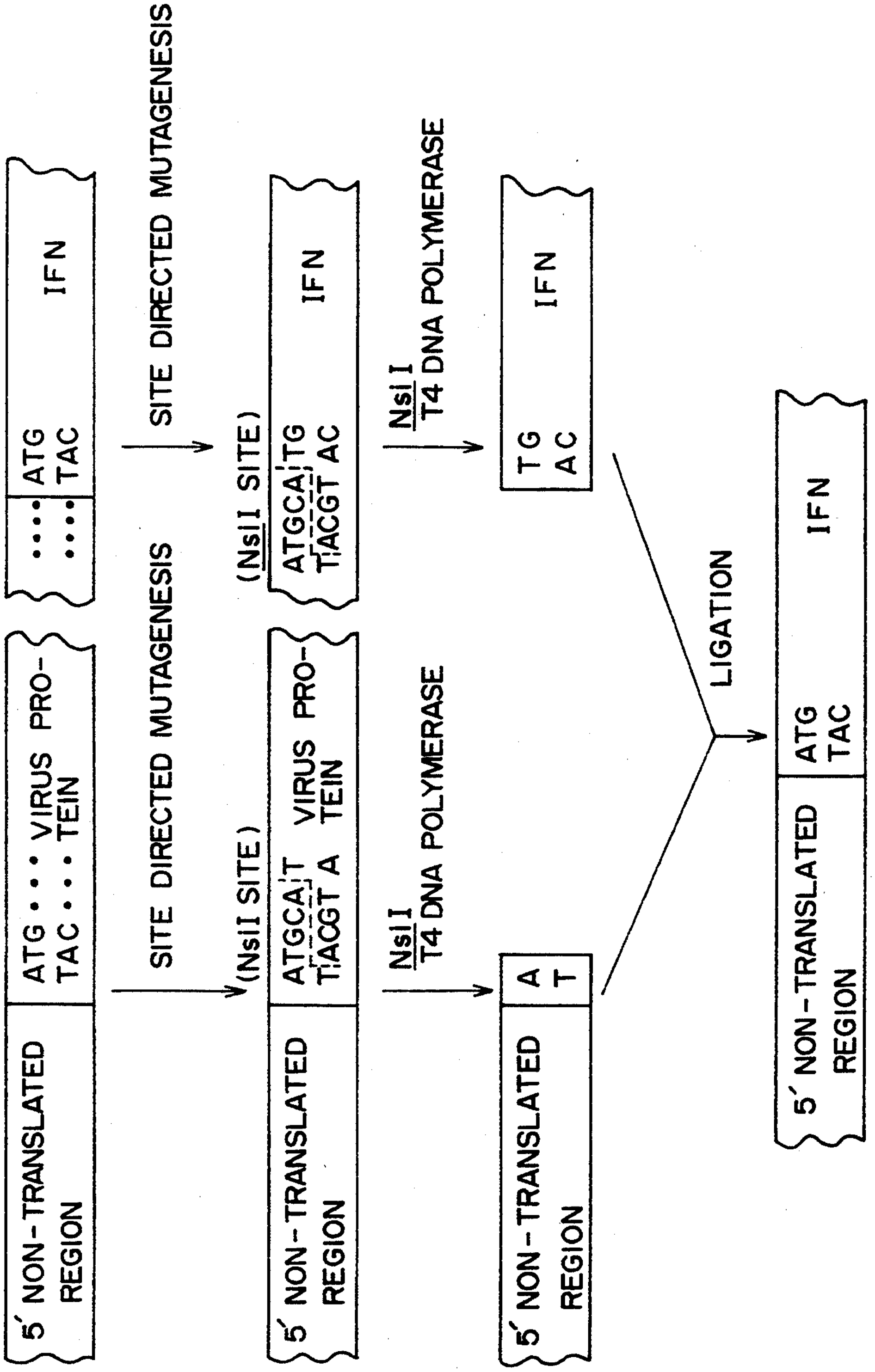

FIG. 4 shows a method for replacing the BMV gene with an exogenous gene.

Figure 5:
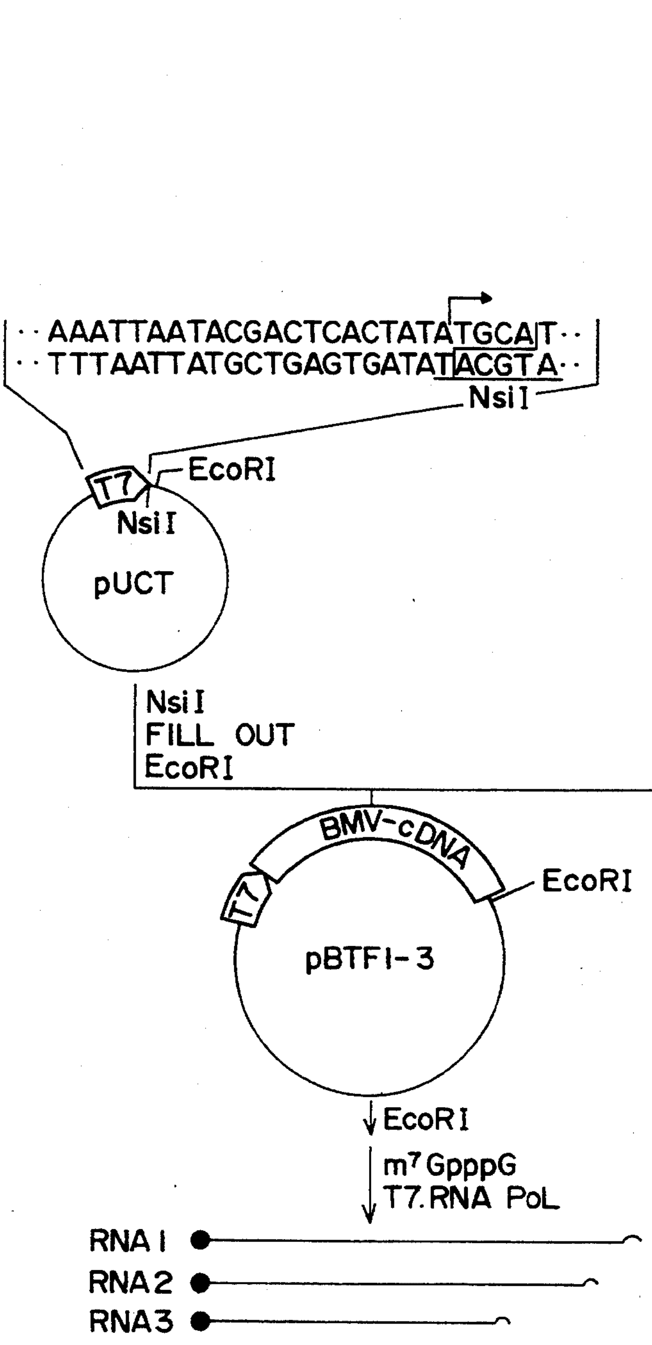

FIG. 5 shows introduction of completely full length cDNA of BMV RNA into transcription vector (pUCT) and the synthesis of BMVRNA in vitro using T7 RNA polymerase.

T7:T7 promoter

↱: transcription initiation site and transcription direction mGpppG: Cap analog

●: Cap structure

⌒: superfluous base added 3′ of BMV RNA

Figure 6:
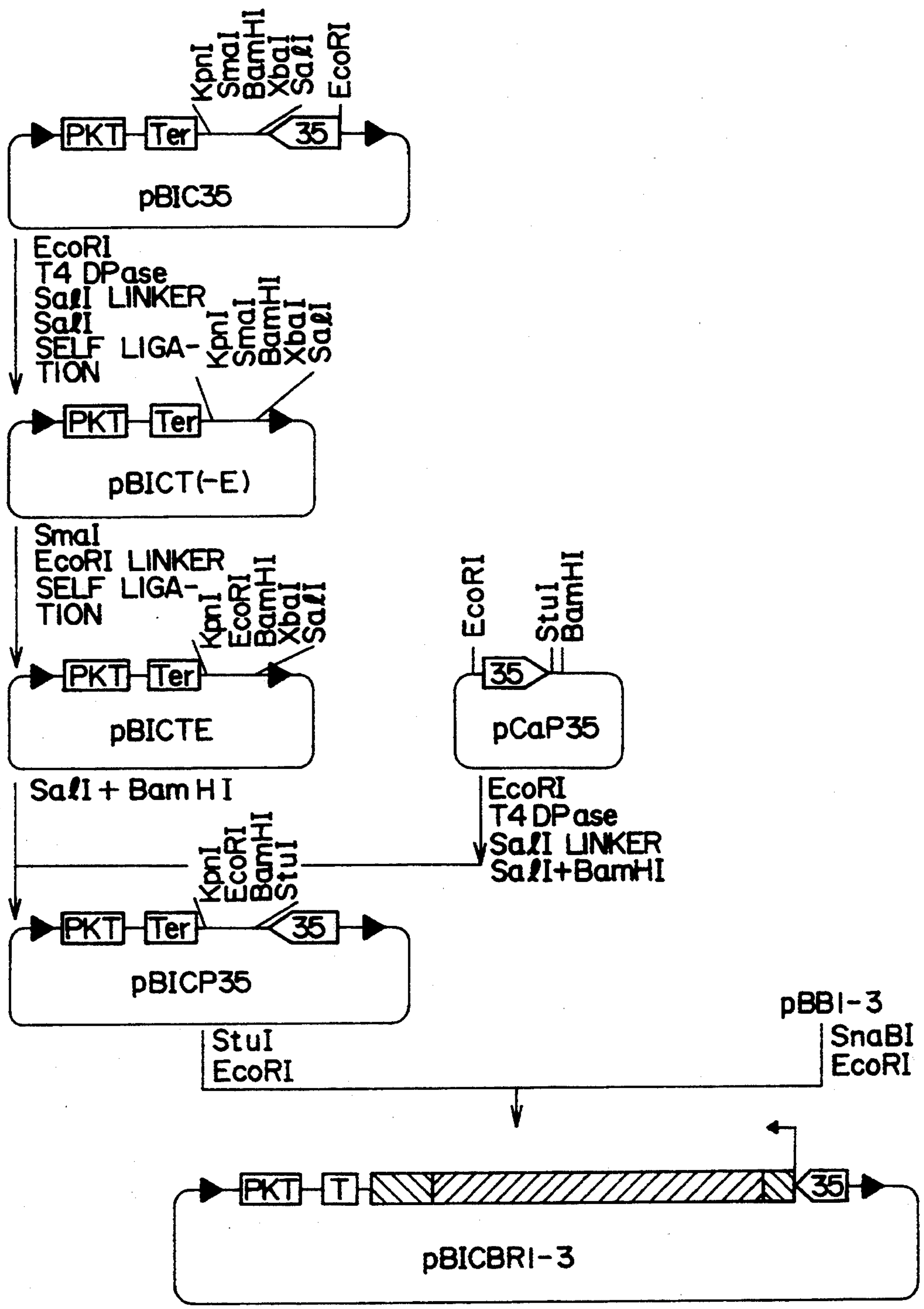

FIG. 6 shows construction of a plant transformation vector pBICBR1-3 in which full length cDNA of BMV RNA was inserted.

PKT: NOS promoter, kanamycin-resistant gene and NOS terminator

35: CaMV35S promoter

T: CaMV terminator

▸: T-DNA border sequence of Ti plasmid

▧: cDNA corresponding to non-translated region of BMV RNA

▨: cDNA corresponding to translated region of BMV RNA

↱: transcription initiation site and transcription direction

Figure 7:
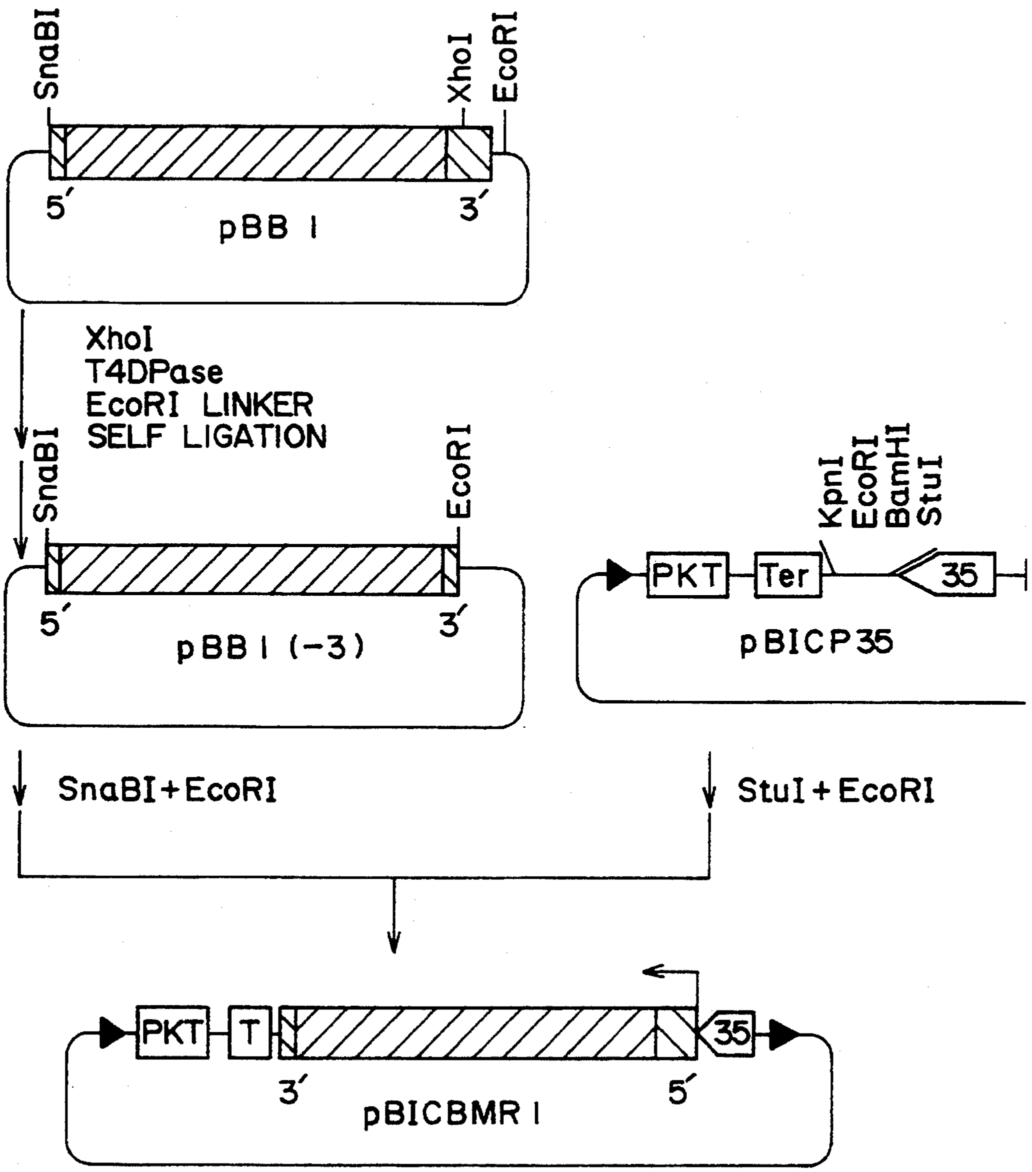

FIG. 7 shows construction of a plant transformation vector pBICBMR1 in which cDNA of BMV RNA with a deletion at the nucleotide site corresponding to 3′ non-translated region of BMV RNA was inserted.

PKT: NOS promoter, kanamycin-resistant gene and NOS terminator

35: CaMV35S promoter

T: CaMV terminator

▸: T-DNA border sequence of Ti plasmid

▧: cDNA corresponding to non-translated region of BMV RNA

▨: cDNA corresponding to translated region of BMV RNA

↱: transcription initiation site and transcription direction

Figure 8:
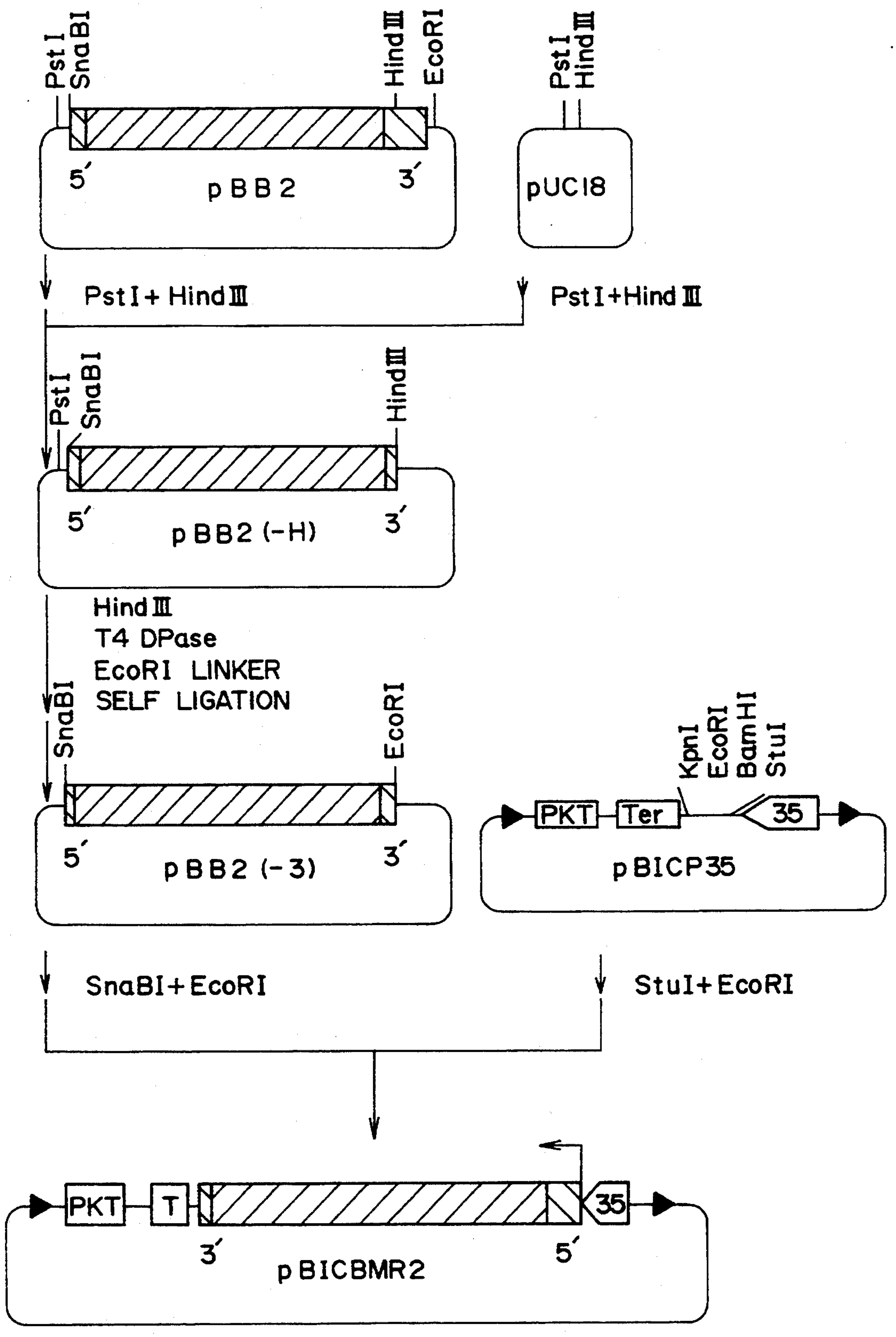

FIG. 8 shows construction of a plant transformation vector pBICBMR2 in which cDNA of BMV RNA with a deletion at the nucleotide site corresponding to the 3′ non-translated region of BMV RNA was inserted.

Figure 9:
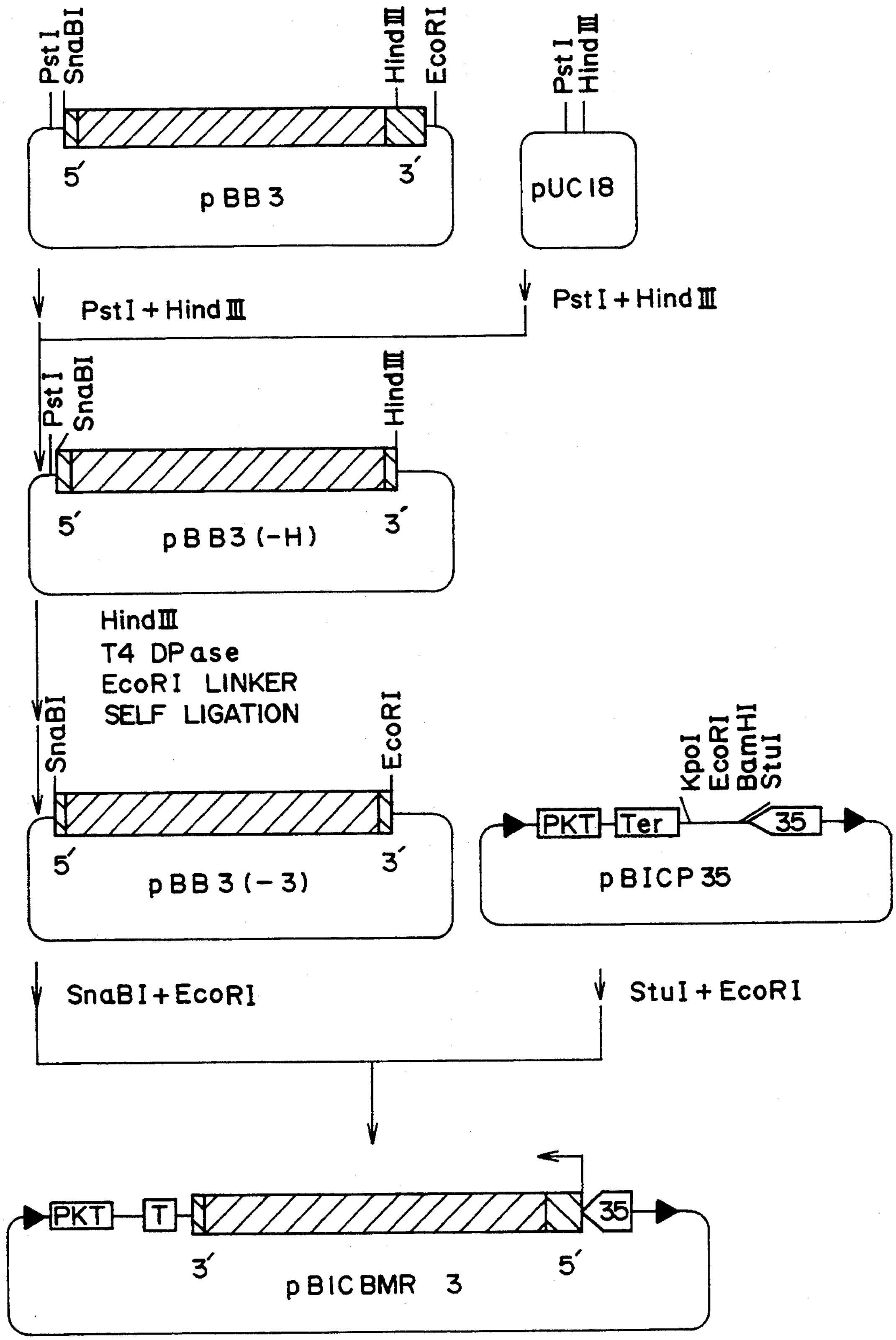

FIG. 9 shows construction of a plant transformation vector pBICBMR3 in which cDNA of BMV RNA with a deletion at the nucleotide site corresponding to the 3′ non-translated region of BMV RNA was inserted.

Figure 10:
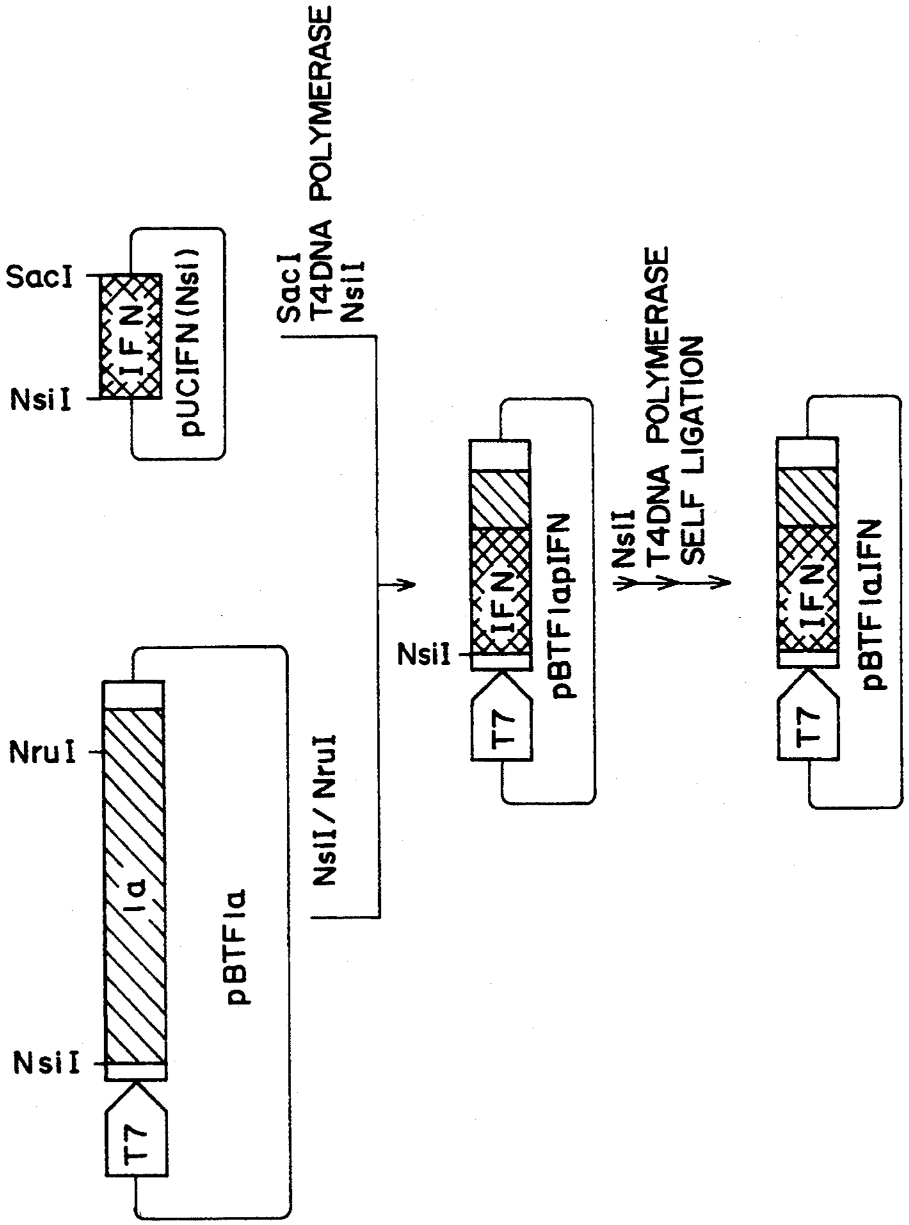

FIG. 10 shows construction of pBTF1aIFN.

Figure 11:
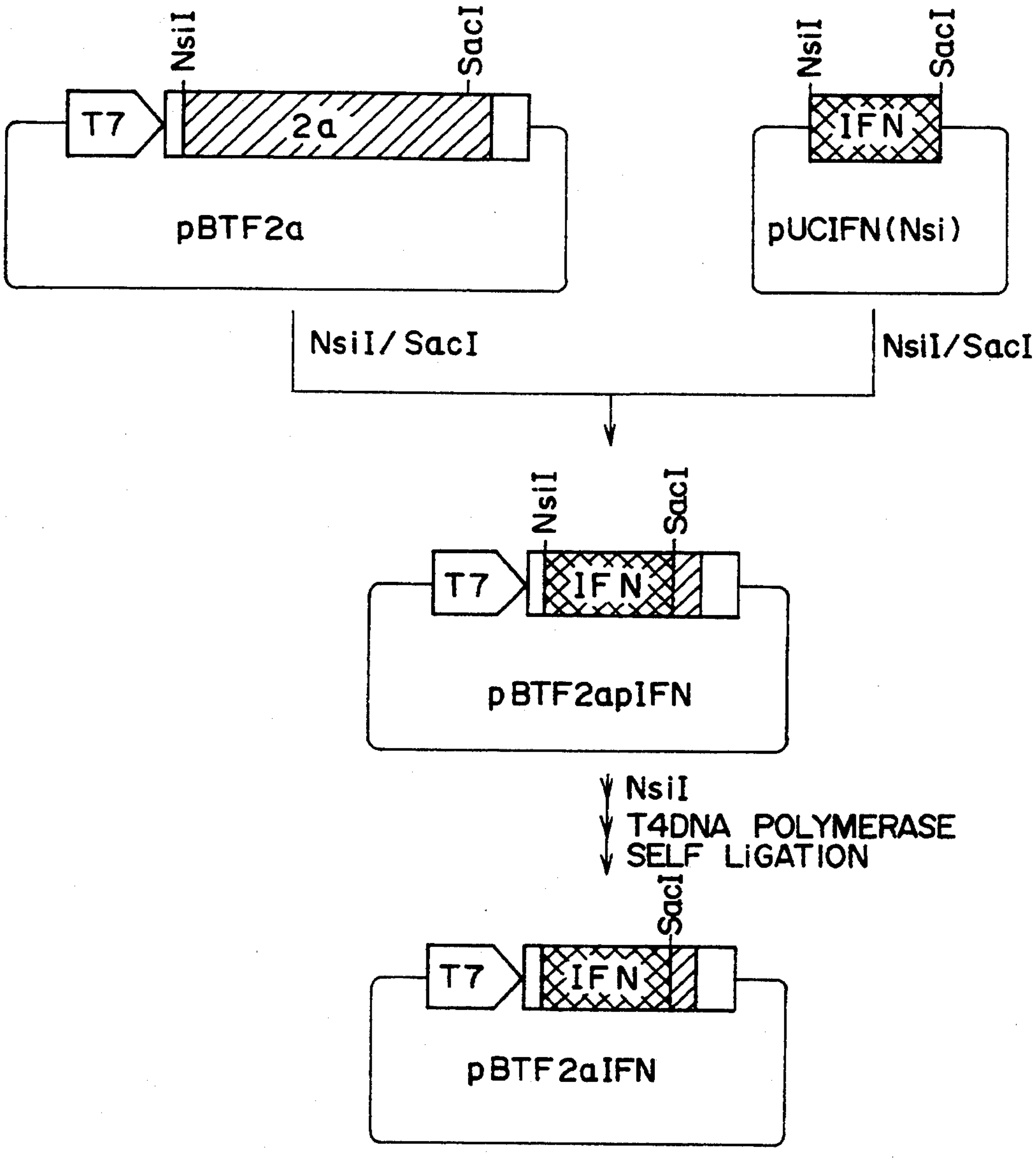

FIG. 11 shows construction of pBTF2aIFN.

Figure 12:
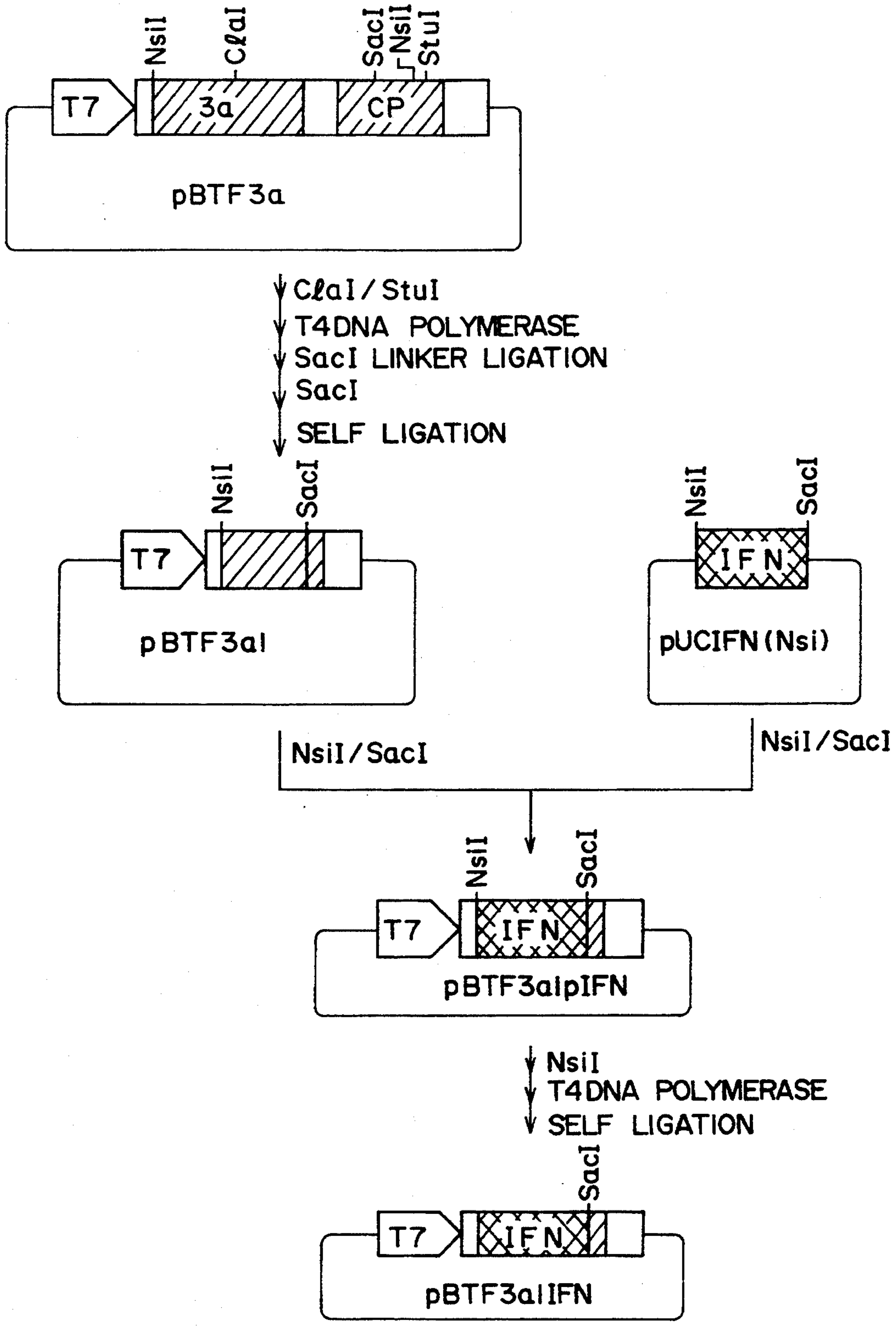

FIG. 12 shows construction of pBTF3a1IFN.

Figure 13:
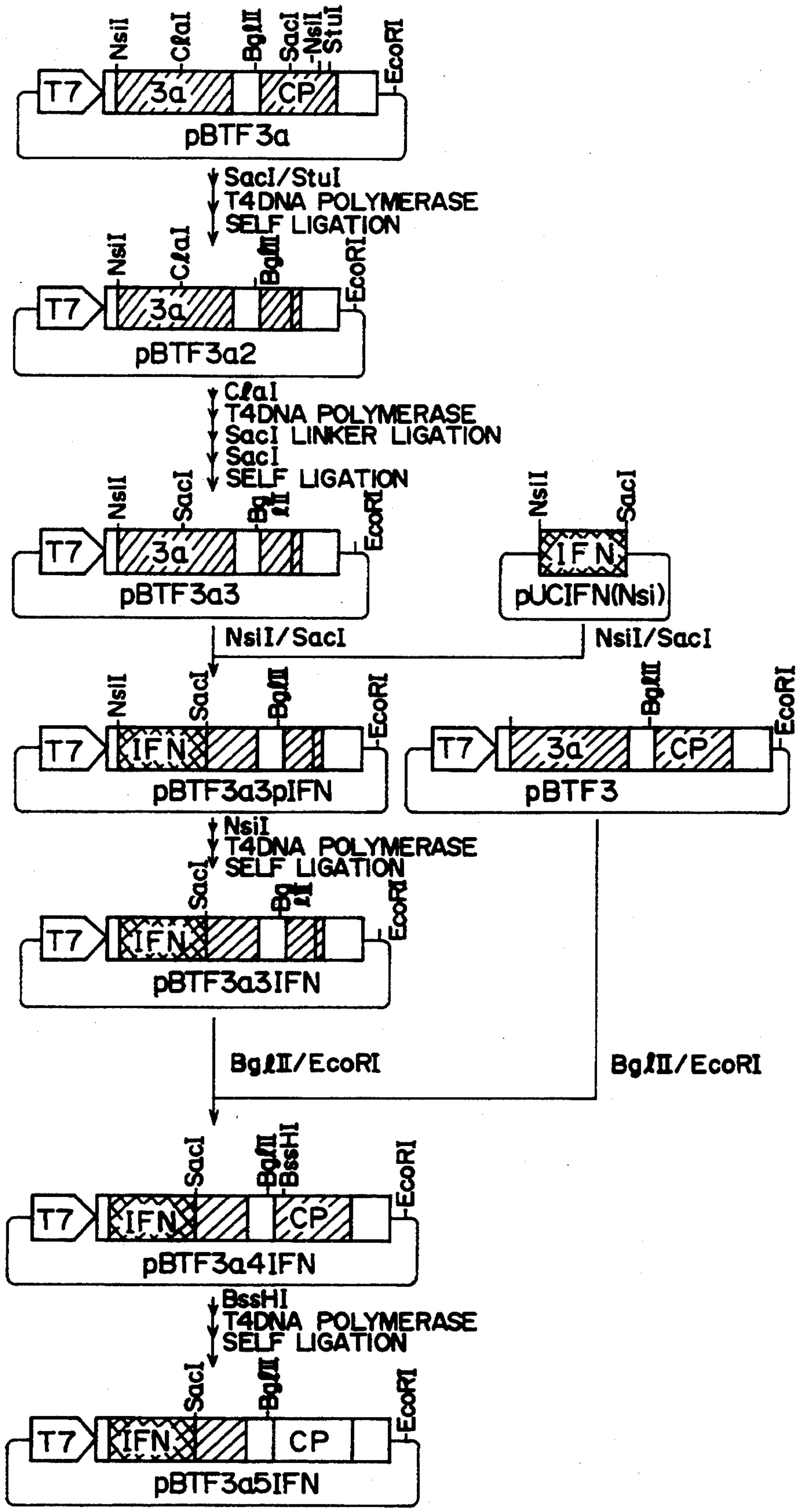

FIG. 13 shows construction of pBTF3a4IFN and pBTF3a5IFN.

Figure 14:
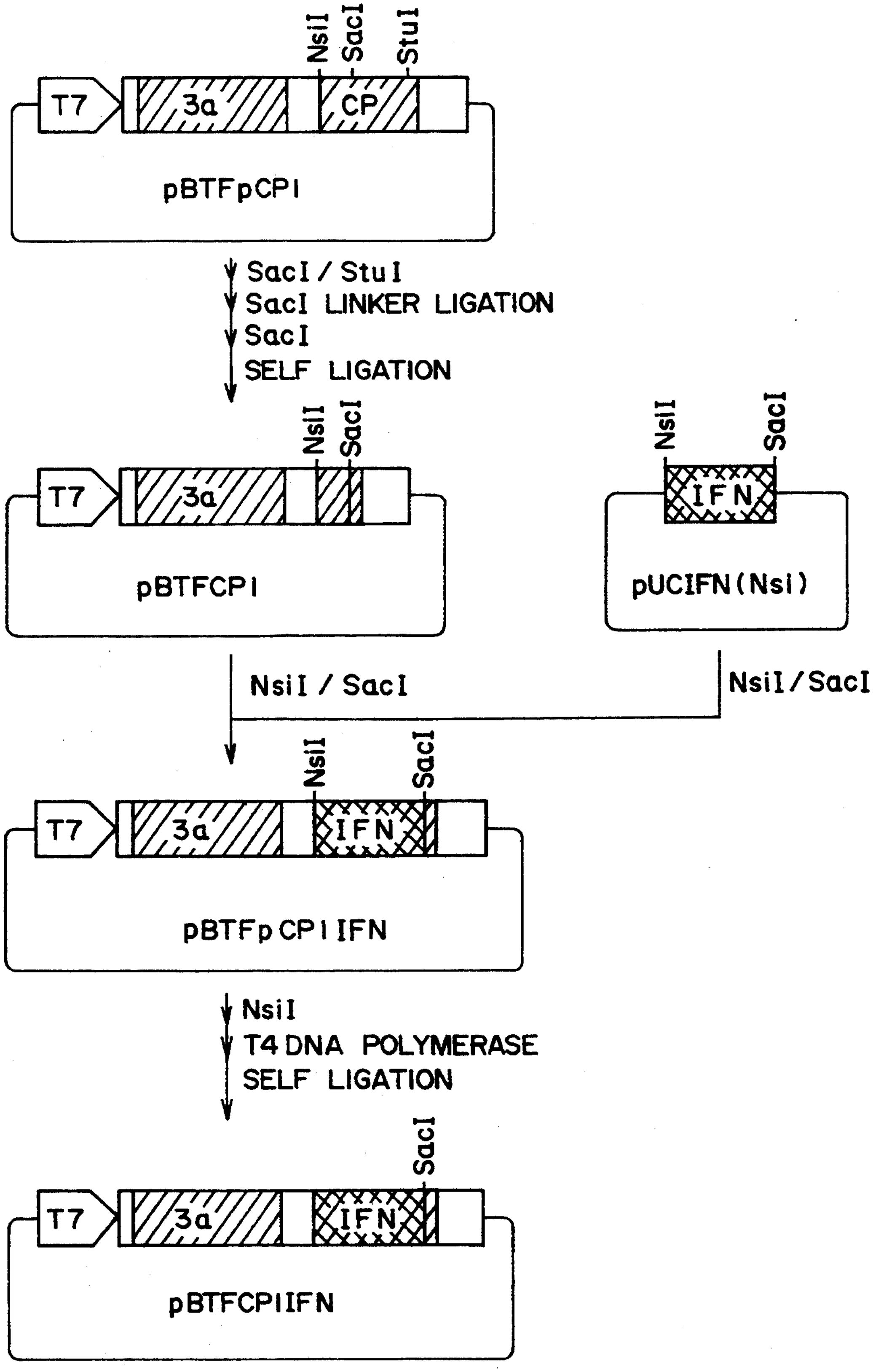

FIG. 14 shows construction of pBTFCP1IFN.

Figure 15:
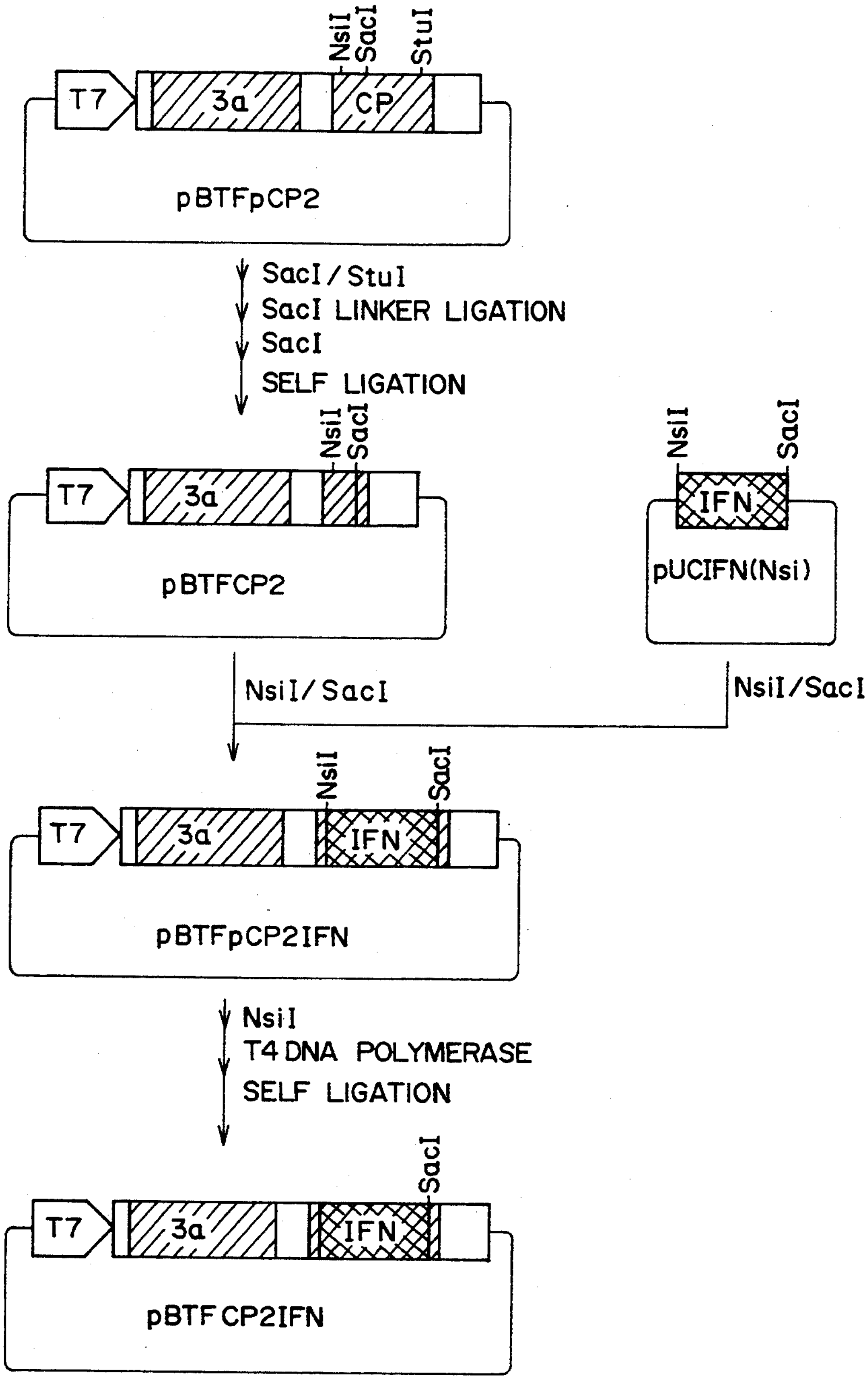

FIG. 15 shows construction of pBTFCP2IFN.

Figure 16:
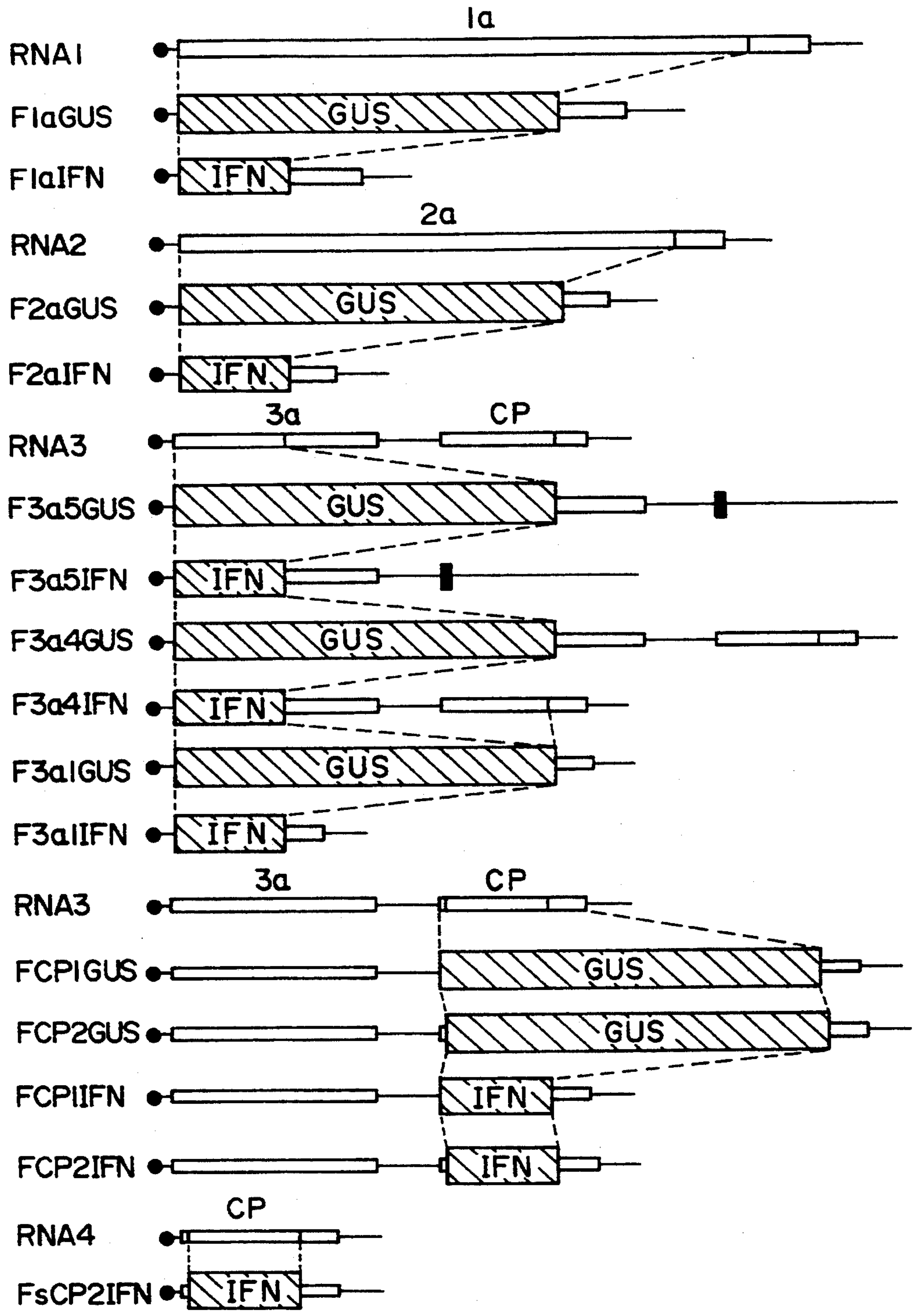

FIG. 16 shows a schematic figure of BMV-IFN chimera RNA and BMV-GUS chimera RNA.

Figure 17:
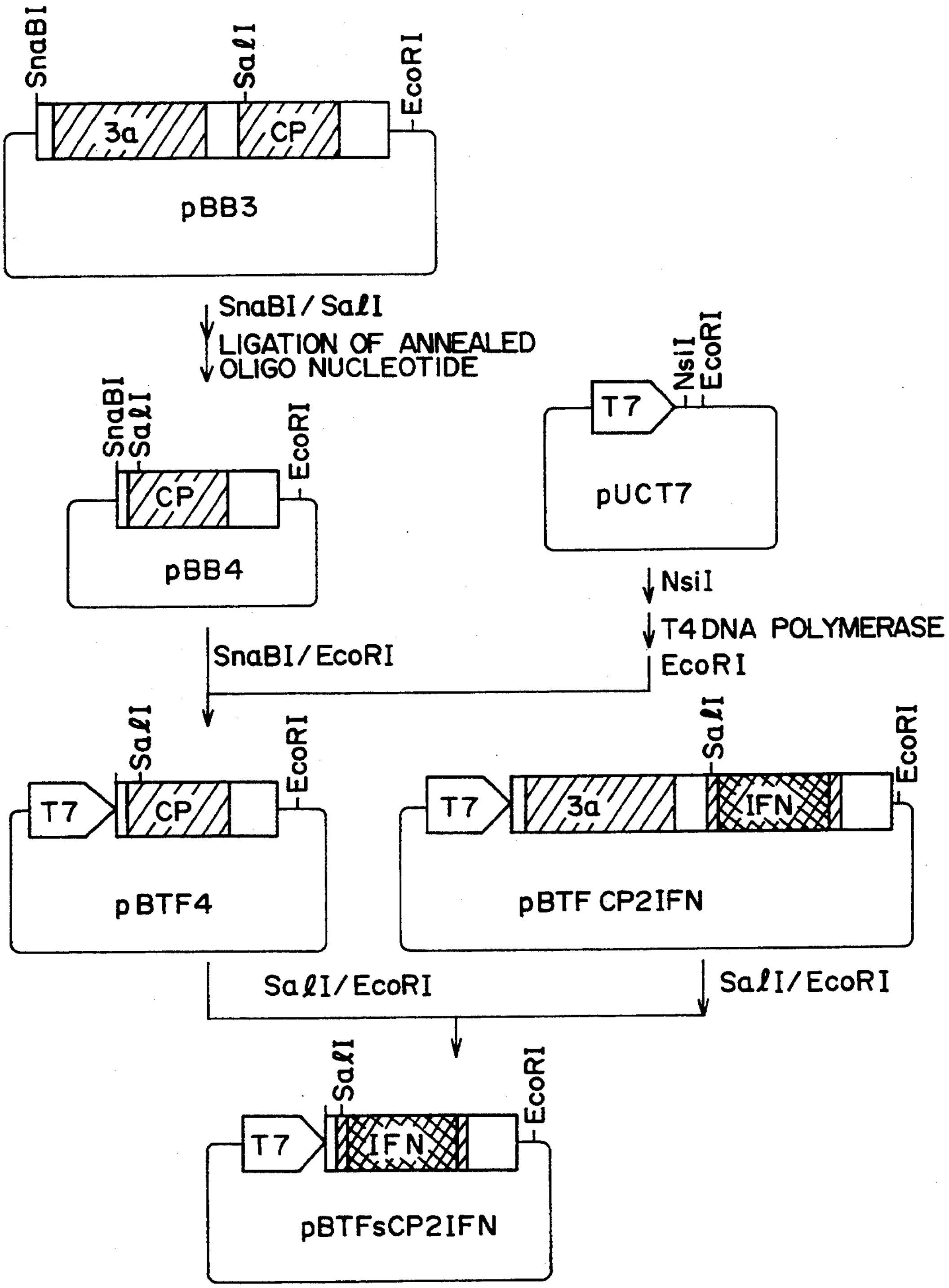

FIG. 17 shows construction of pBTFsCP2IFN.

Figure 18:
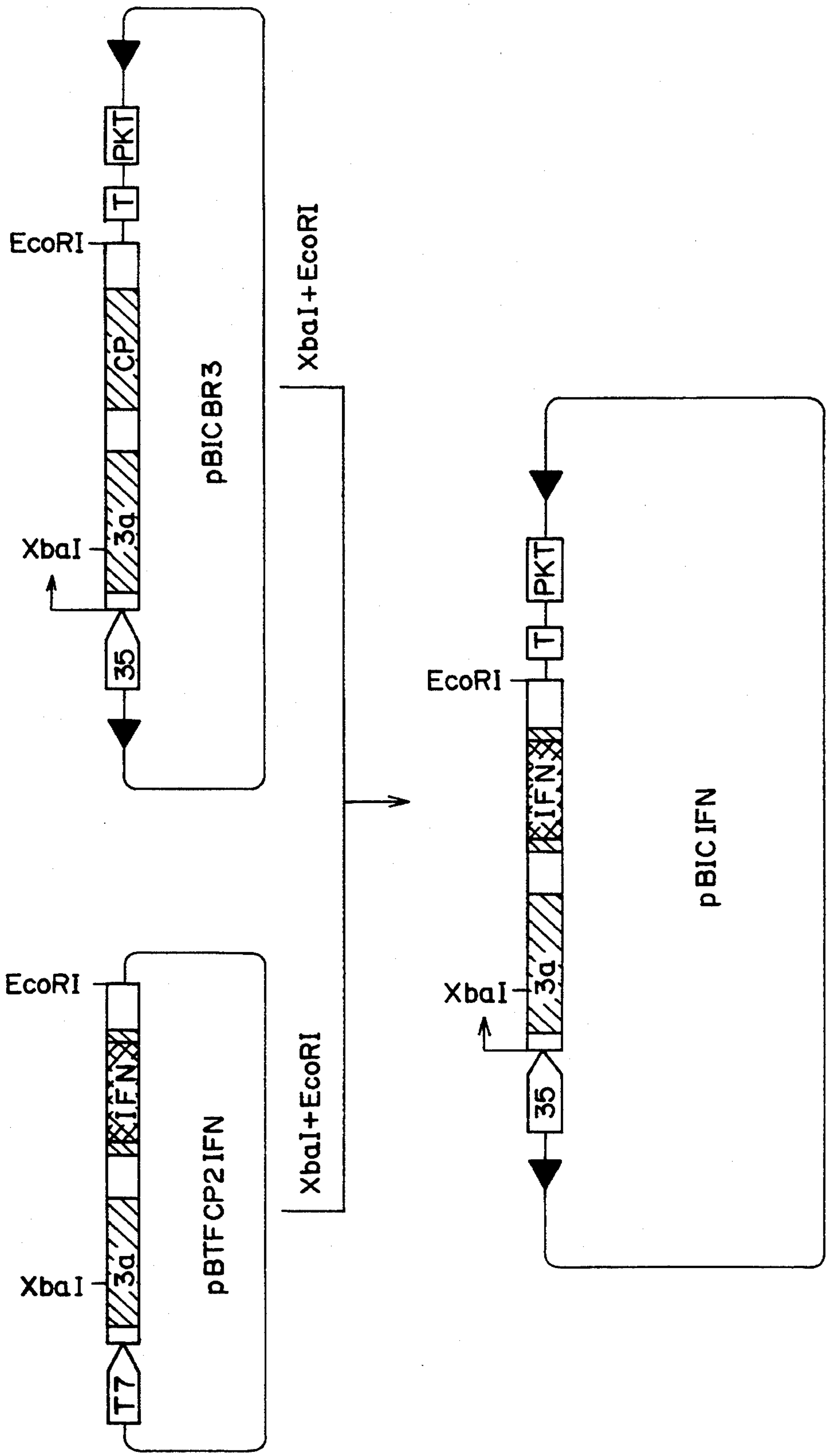

FIG. 18 shows construction of a plant transformation vetor pBICIFN in which BMV-IFN chimera RNA3 cDNA has been inserted.

PKT: NOS promoter, kanamycin-resistant gene and NOS terminator

35: CaMV35S terminator

T: CaMV terminator

▸ : T-DNA border sequence of Ti plasmid

↱ : transcription initiation site and transcription direction

DETAILED DESCRIPTION OF THE INVENTION

The present inventors have inserted exogenous gene into almost all sites in plant virus genome which can be seen, and compared the production amounts of the exogenous gene products. As a result, when the nucleotide moiety at and after ATG downstream from the original translation initiation codon (the first ATG counted from the 5′-end) in cDNA of virus coat protein gene is replaced with desired exogenous gene, it has been revealed that unexpected high efficient production of the exogenous gene products was done. The present invention is based upon this finding.

(1) RNA Plant Virus

The RNA plant virus which can be used in the present invention is preferably composed of (+)-stranded RNA where the virus genomes are present, more preferably BMV, CMV and AMV.

The genomic RNAcDNA containing the replicase genes of these viruses are inserted into the genome of a plant cell. The genomic RNAcDNA containing the coat protein gene in which an exogenous gene has been incorporated are inserted into the genome of a plant cell or a plant cell is inoculated with RNA synthesized in vitro.

Figure 1:
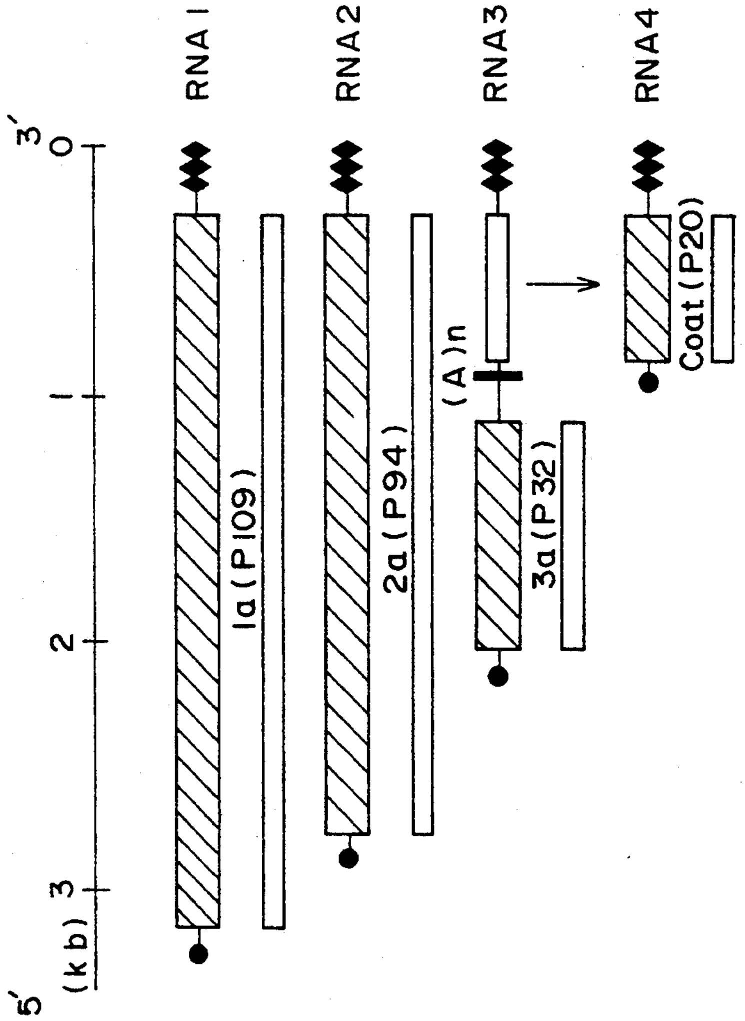
FIG. 1 shows a mode for gene expression of BMV.

In the case of BMV, CMV and AMV, the genome consists of four kinds of RNAs (FIG. 1) and these viruses are handled most easily in the present invention. However, as long as the replicase gene and the coat protein gene of other viruses can be inserted into the genome of a plant cell such that each of these genes can be expressed independently, the present invention is applicable to such viruses.

Taking BMV, CMV and AMV examples, the moieties to be modified in the present invention for the purpose of inserting them into the plant genome are RNA1, 2 and 3. In the modified RNA3, the coat protein gene portion encoded at the 3′ side is replaced by a desired exogenous gene.

Examples of suitable plants into which the virus genome can be inserted are tobacco, soybean, cucumber, potato, rice, wheat, barley, corn, etc.. It should be understood that the present invention is not limited to these plants.

In the plant viruses described above, plants which become hosts of the respective viruses are different. For example, many plants belonging to Gramineae can be hosts of BMV. In inoculation of virus particles or virus RNA on tobacco plants, however, BMV does not multiply in these plants. It is thus considered that tobacco is not a suitable host for BMV. However, it is reported that when a tobacco protoplast is inoculated with BMV particles or virus RNA, RNA is replicated in the cells and production of coat protein is induced (Maekawa et al., *Ann. Phytopath. Soc. Japan* (1985), 51:227-230). Thus, if a virus gene can be expressed in plant cells, it is not necessary to be bound by the conventional relationship between virus and host.

According to the present invention, plants to which the present invention is applicable can be chosen without being bound to the conventional concept of virus and host, even in the case of inserting a virus gene into the genome of a plant cell. Plant cells as used herein include protoplasts.

(2) Construction of Plant Transformation Vector

Virus RNA is extracted from virus particles by known techniques for extracting RNA, for example, the guanidine method, the hot phenol method, sodium lauryl sulfate (SDS) phenol method, etc. In the case of BMV, CMV and AMV, the genome consists of several kinds of RNAs and the RNAs are fractionated and purified as RNAs 1, 2 and 3. Construction of the complementary DNA (cDNA) corresponding to each RNA can be achieved by utilizing conventional genetic manipulation techniques (Ahlquist et al., *J. Mol. Biol.* (1984), 172:369-383; Mori et al., *J. Gen. Virol.* (1991), 72:243-246).

In the present invention, in the case of genomic RNA containing the replicase gene, for example, BMV, CMV and AMV, RNAs 1 and 2 are inserted into the genome of a plant cell, respectively, as a DNA molecule comprising a) a promoter which functions in a plant cell, b) cDNA of RNAs 1 or 2, and c) a terminator which functions in a plant cell. In the transformed plant cell in which such a DNA molecule has been inserted, RNAs 1 or 2 are transcribed and 1a and 2a proteins are produced. The coat protein gene region of RNA3 cDNA is replaced with a desired exogenous gene to construct recombinant RNA3cDNA.

The recombinant is then inserted into the genome of a plant cell, in which the 1a and 2a proteins described above are expressed, as a DNA molecule comprising a) a promoter which functions in a plant cell, b) recombinant RNA3cDNA, and c) a terminator which functions in a plant cell. Alternatively, a plant cell is inoculated with recombinant RNA3 produced in vitro using the transcription vector, in which the 1a and 2a proteins described above are expressed.

Figure 2:
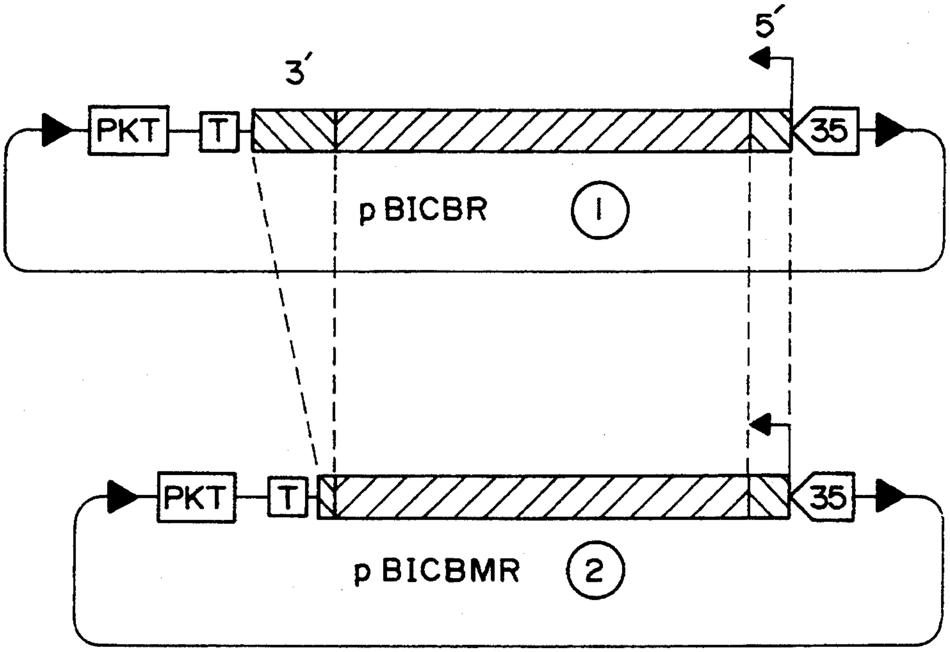
FIG. 2 shows a tobacco transformation vector in each gene of BMV.

The transformation vector used to insert the DNA molecule comprising a) a promoter which functions in a plant cell, b) cDNA of RNAs 1 or 2, and c) a terminator which functions in a plant cell, into a genome of a plant cell can be two kinds of vectors, for example, type (1) (pBICBR vector) and type (2) (pBICBMR vector) shown in FIG. 2 of the accompanying drawings. The two vectors possess the complete 1a and 2a translation region. In addition, type (1) vector bears cDNA of the full 5′ and 3′ non-translated regions of virus RNA; whereas type (2) vector bears cDNA of the full 5′ non-translated region but cDNA at the nucleotide portion corresponding to the 3′ non-translated regions is deleted. The 5′ non-translated regions of virus RNA are essential for translation efficiency and the synthesis of (+)-strand from the (−)-strand, and the 3′ non-translated region is essential for the synthesis of the (−)-strand from the (+)-strand. Therefore, the deletion of the 3′ non-translated region results in a deletion of the synthesis of the (−)-strand from the (+)-strand and thus a loss in the multiplication efficiency of virus RNA but does not affect the translation efficiency thereof. Where the full length cDNA of virus RNA is inserted into a genome of a plant cell using type (1) vector, the transcription product produced in the transformed cells multiplies as in the wild type of virus RNA and also translation occurs. On the other hand, where the 3′ end-deleted cDNA of virus RNA is inserted into a genome of a plant cell using type (2) vector, the transcription product produced does not multiply in the transformed cells but translation occurs, whereby the translated product alone is produced. When the virus RNA multiplies in large quantities, it is considered to cause the plant to be diseased and adversely affect growth of the plants. In order to solve the problem, type (2) vector may thus be used.

Examples of the promoter and terminator which function in a plant cell include a promoter functional in a plant cell such as cauliflower mosaic virus (herein after CaMV) 35S promoter and terminator functional in a plant cell represented by CaMV terminator, etc.

It has been shown that BMV RNA variant having a nucleotide sequence with seven superfluous nucleotides at the 5′ end lacks infection efficiency (Janda et al., *Virology* (1987), 158:259–262). Therefore, in order to impart translation efficiency to the nuclear transcription product of the full length cDNA of virus RNA inserted into a plant cell, it is necessary to accurately coincide the transcription initiation site of cDNA with the 5′ end of the virus RNA. In the case of using CaMV 35S promoter, cDNA of the transcription initiation site needs to be introduced immediately downstream of the transcription site (FIG. 3). The moieties which can be replaced with a desired exogenous gene are moieties of 1a protein, 2a protein, 3a protein and moieties from the first translation initiation codon in the coat protein gene, or on and after the first translation initiation codon in the coat protein gene, for example, from the second and third, etc. In order to insert the desired exogenous gene into these sites, NsiI restriction sites are introduced into both the translation initiation codon (ATG) in the gene to be replaced and the translation initiation codon in the exogenous gene using the Kunkel et al. method (Kunkel et al, *Methods in Enzymology* (1987), 154:367–382), and then restricted by NsiI. The single chain moiety is removed by T4DNA polymerase to form a blunt end, and ligated, and the replacement of the exogenous gene can be performed without modifying the reading frame (in frame) (FIG. 4).

(3) Preparation of Transformant by Plant Transformation Vector

As the plant transformation method using *Agrobacterium tumefaciens*, the leaf disc method (Horsch et al., *Science* (1985), 227:1229–1231) is most generally utilized. Ti plasmid has a vir region and by the action of this region, the T-DNA region in the Ti plasmid can be inserted into a genome of a host cell of *A. tumefaciens* (Nester et al., *Ann. Rev. Plant Physiol.* (1984), 35:387–413). Gene introduction techniques using Ti plasmid include the binary vector method which has been widely used. According to this method, Ti plasmid is divided into a binary vector of T-DNA-deleted Ti plasmid with the vir region and Ti plasmid containing T-DNA, and the binary vector is used. The binary vector is a vector which can multiply both in *A. tumefaciens* and *E. coli*. DNA composed of the promoter, virus RNAcDNA and the terminator is incorporated into the T-DNA region in the binary vector to construct a transformation vector. Such a transformation vector is introduced into *A. tumefaciens* cells carrying T-DNA-deleted Ti plasmid with a vir region and a host plant is inoculated with this *A. tumefaciens*. By the action of vir region, the DNA-containing T-DNA region composed of this combination can be inserted into the genome of a host cell. The DNA having the above-described construction may also be inserted into the genome of a plant cell using other known gene introduction techniques, namely, electroporation into a protoplast, liposome fusion, microinjection, particle gun into a plant tissue or the like.

For selection of the transformant, chemical agents such as kanamycin, hygromycin, phosphinothricin, etc., may be used. The transformant may be cultured in an appropriate medium to form a callus, the callus allowed to proliferate, if necessary and desired, adventitious embryo differentiation or organ differentiation permitted and then regenerated into a plant in a plant regeneration medium supplemented with a plant hormone.

Where the present invention is applied to a dicotyledonous plant, suitable examples of plants include Leguminosae (alfalfa, soybean, clover, etc.), Umbelliferae (carrot, celery, etc.), Cruciferae (cabbage, radish, rapeseed, etc.), Solanaceae (potato, tobacco, tomato, etc.) and the like. Where the present invention is applied to a monocotyledonous plant, *A. tumefaciens* technique can not be utilized but it is possible to utilize electroporation into a protoplast, liposome fusion, micro injection or particle gun into plant tissue. Examples of suitable plants include Gramineae (rice, wheat, barely, corn, etc.).

To obtain a transformed cell with introduced cDNA of RNAs 1 and 2 inserted into the genome using a type (1) or type (2) vector, (1) the transformed plant in which RNA1cDNA has been inserted is hybridized with the transformed plant in which RNA2cDNA has been inserted, and a plant which produces 1a and 2a proteins is selected. Alternatively, (2) the same plant is transformed by a vector containing RNA1cDNA and a vector containing RNA2cDNA, which have selection markers of different chemical resistance, (3) co-transformation is performed in the same cell using the electroporation method; and the like. Production of 1a and 2a proteins may be confirmed by inoculating the protoplast obtained from the transformed plant with RNA3 plant and the presence of coat protein by Western blotting. Further in order to obtain the pure line plant homologously having both cDNA of RNA1 and RNA2 in the genome of a plant cell, the transformed plant which produces 1a and 2a proteins is subjected to anther culture, and the chromosome of the haploid plant derived from pollen is doubled to obtain pure line diploid. Then, by the technique described above, the transformed plant which produces 1a and 2a proteins may be selected.

(4) Construction of Recombinant Virus Genomic RNA Transcription Vector

In the present invention, DNA which encodes a desired polypeptide to be produced may also be recombined into a transcription vector for producing the transcription product in vitro and produced as RNA using the recombinant transcription vector.

In order to synthesize virus RNA in vitro, DNA-dependent RNA polymerase may be used. Examples of DNA-dependent RNA polymerase include T7 RNA polymerase, SP6 RNA polymerase and *E. coli* RNA polymerase, etc., which are commercially available. T7 RNA polymerase in which the nucleotide sequence in the promoter region and the transcription initiation site have been accurately determined and has a high transcription efficiency (Dunn et al., *J. Mol. Viol.* (1983), 166:477–535) may be advantageously used. The structure of 5′ region of virus RNA has a very important role in replication of virus RNA, translation, etc. It is reported that when a superfluous nucleotide sequence is added to the 5′ end, the biological activity of the virus RNA is drastically reduced (Janda et al., *Virology*

(1987), 158:259–262). For this reason, in order to synthesize virus RNA having the same 5′ nucleotide sequence as that of the wild type in vitro, it is preferred that transcription be initiated accurately from the base of the DNA corresponding to the 5′ end of virus RNA. Therefore, taking BMV as an example, BMV RNA3 transcription vector pBTF3 is constructed (Mori et al., *J. Gen. Virol.* (1991), 72:243–246, U.S. patent application Ser. No. 07/663,164) (FIG. 5).

pBTF3 vector can utilize a material for constructing the recombinant BMV RNA3 transcription vector, pBTF3 vector comprises T7 promoter, BMV RNA3cDNA and the gene of pUC vector which is a vector for *E. coli*. NsiI restriction sites are introduced into the translation initiation codon in the coat protein gene of the above mentioned vector using the Kunkel et al. Method, and a linker, etc., is ligated at the stuI restriction enzyme site present in the coat protein gene portion of the vector described above to replace with the SacI restriction enzyme site, NsiI/SacI fragments are removed and NsiI/SacI fragment containing the exogenous gene is incorporated and thus the exogenous gene can be introduced without changing the reading frame.

In production of the transcription product, recombinant pBTF3 vector is digested with EcoRI to form a linear DNA product. Using this DNA as a template, recombinant RNA3 is produced in large quantities by the in vitro transcription system involving ATP, UTP, CTP, GTP, Cap analog (m7GpppG) and T7 RNA polymerase.

(5) Expression of Exogenous Gene in Transformant Protoplast Capable of Producing Replicase In a transformant with a replicase gene, for example, both cDNA of RNAs 1 and 2 inserted into a genome, replicase having a biological activity, for example, 1a and 2a proteins are produced in all of the cells. That is, virus genome can be expressed in such a transformant using the mechanism of transcription and translation of a plant. Furthermore, recombinant virus genomic RNA such as recombinant RNA3cDNA, is inserted into the genome of a transformant having both cDNA of RNAs 1 and 2 inserted in the genome, using a transformation vector; recombinant RNA3 is transcribed by the transcription mechanism of the plant so that recombinant virus genomic RNA such as recombinant RNA3 is replicated by replicase, e.g., la and 2a proteins produced in the plant cell. At the same time, recombinant RNA4, which is a subgenome, is also synthesized in large quantities. The presence of the DNA of the recombinant virus genomic RNA, e.g., RNA3 cDNA in the genome of the transformed plant can be confirmed by Southern blotting; production of recombinant RNA3 and recombinant RNA4 can be confirmed by Northern blotting; and production of the exogenous gene product can be confirmed by Western blotting with anti-INF antibody, where, e.g., human-derived γ-interferon (hereinafter referred to IFN) is introduced. In case that β-glucuronidase (hereinafter referred to as GUS) is used as the exogenous gene, production of the exogenous gene products can be confirmed by the spectrophotometric determination method generally used (GUS gene fusion system users manual).

It has been already confirmed that in a transformed plant cell in which RNA1cDNA, RNA2cDNA and recombinant RNA3 DNA are introduced into the genome of the plant, β-glucuronidase is produced when β-glucuronidase, for example, is used as an exogenous gene (U.S. patent application Ser. No. 07/663,164). Therefore, the comparison of gene expression efficiency to determine the replacement site for an exogenous gene can be performed more easily, accurately and reproducibly either by a) the synthesized recombinant RNA is inoculated into a protoplast of the transformed plant in which RNA1cDNA and RNA2cDNA are inserted into the genome, or b) the synthesized RNA1, RNA2 and recombinant RNA are inoculated at the same time, than by studying the plant in which three of RNA1cDNA, RNA2cDNA and recombinant RNAcDNA replaced with exogenous gene are introduced into a genome of the plant. Because, when recombinant RNAcDNA is introduced into the genome of the plant, the quantity of recombinant RNA transcribed in the cell varies based on the site and number introduced. Known methods, such as the polycation method, the polyethylene glycol method and the electroporation method, etc., can be used as the introduction method.

BMV produces 1a, 2a, 3a and coat protein. Further, it is known that, depending on the strain, a coat protein of 19 KD (CP2) is also produced in addition to a coat protein of 20 KD (CP1) (Sacher and Ahlquist, *J. Virol.* (1989), 63:4545–4552). The present inventors have found that surprisingly, the amounts of the exogenous gene products increase by leaps when CP2 is replaced with an exogenous gene, as a result of studying the relationship between the amounts of an exogenous gene produced and the replacement site for the exogenous gene, using ATCC66 strain and by replacing a portion from the first translation initiation codon or a portion on and after the first translation initiation codon in the cDNA of the coat protein gene with the desired exogenous gene. While not desiring to be bound, the present inventors believe that the nucleotide sequence from the 5′ end non-translated region in the cDNA of the above coat protein to the second translation initiation codon in the coat protein structural gene is important. The sequence has been determined to be 5′GTATTTAATGTCGACTTCAGGAACTGGTAAGATG (Seq. ID. No.: 1). That is, there is the possibility that the nucleotide sequence around the first translation initiation codon from the nucleotide portion corresponding to the 5′ non-translated region in cDNA of ATCC66 coat protein gene has an improper structure for translation, and the nucleotide sequence around the second translation initiation codon has the proper structure for translation. As a result, translation starts from the second translation initiation codon and this makes the translation efficiency from CP2 of ATCC66 higher.

Furthermore, the present invention provides an excellent advantage that a desired exogenous gene product can be produced in large quantities and such is not a fusion protein with a coat protein. From the above, according to the present invention, even with other plant viruses, it is possible to increase the production of the desired exogenous gene product by conducting such a genetic technique as deletion or replacement, etc., using site directed mutagenesis by the Kunkel et al. method (Kunkel et al., *Methods in Enzymology* (1987), 154:367–382), etc., at the nucleotide portion corresponding to 5′non-translated region of coat protein gene cDNA. By conducting such genetic technique as the nucleotide sequence around the first translation initiation codon is modified to make the improper structure for translation, and the nucleotide sequence around the second translation initiation codon is modified to make a proper structure for translation, the translation is started from the second translation initiation codon. Further, it is possible to artificially produce an ATG site downstream from the original translation initiation site in order to start the translation from the artificially produced ATG site.

According to the inoculation method, it is impossible to express the exogenous gene in the entire plant body, because the coat protein gene portion which is necessary in transporting the viruses into the entire plant body is removed in the recombinant RNA (Allison et al. *Proc. Natl. Acad. Sci. USA* (1990), 87:1820–1824). In the present invention, it becomes possible to express the exogenous gene in the entire plant body, because in the present invention the recombinant RNAcDNA is further introduced into the transformed plant in which cDNA of the RNA replicase gene is introduced into the genome of the plant, and the exogenous gene is expressed in the entire transformed plant.

The process of the present invention enables the gene product to be efficiently produced by inserting the virus replicase gene coded for in the genome of RNA plant virus into the genome of a plant cell, producing the replicase by the mechanism of transcription and translation in the plant, and synthesizing mRNA of a desired gene in the plant cell in large quantities, which provides high translation efficiency. Therefore, the present invention is extremely valuable from an industrial standpoint. According to the process of the present invention, (1) the exogenous gene is incorporated into a plant transformation vector after the gene is wholly or partly recombined with the coat protein gene of virus genomic RNA. This is then introduced into the plant genome, transcribed as recombinant RNA in the plant cell or (2) the exogenous gene is incorporated into a transcription vector after recombination as described above. Then, the plant is inoculated with the RNA synthesized in vitro from the vector. Thus, the exogenous gene can be utilized extremely efficiently, as compared to the case where all virus genomic RNAs are synthesized in vitro followed by inoculating a plant with them.

Further, as in the case of ATCC66, the present invention is extremely valuable from an industrial standpoint, because a desired exogenous gene product, which is not a fusion protein with a coat protein, is produced in large quantities by conducting modification, such as deletion or replacement, etc., by site specific mutation using the Kunkel et al. method (Kunkel et al., *Methods in Enzymology* (1987), 154:367–382), etc., of the nucleotide sequence from the 5′ non-translated region to the second translation initiation codon of coat protein gene. Further, if at and after the second translation initiation codon in the coat protein gene is taken as a portion to be replaced with the exogenous gene, a desired exogenous gene, the product of which is not a fusion protein with a coat protein, can be produced in large quantities. As the gene introduced into the recombinant virus genomic RNA, for example, recombinant RNA3, a variety of genes are considered. For example, genes of agriculturally useful proteins, functional proteins, proteins used as drugs, e.g., interferon, etc., may be introduced. In these cases, it is possible to introduce the genes even when an active protein is not obtained using a bacterial method, for example, the addition of sugar chain structure is important for activation of the protein and is not possible bacterially.

Furthermore, the present invention can be a very effective method if the protein is toxic and kills animal cells or bacterial cells but is not toxic to plant cells. Further, where the process is applied to breeding of crops, expression of a characteristic can be acquired with a higher frequency, since the amount of mRNA produced by the exogenous gene is larger than the conventional process in which several copies of the exogenous gene are inserted into the genome of a plant cell. In the case where the exogenous gene is, e.g., the coat protein gene of a virus, the process is applicable to breeding of a virus-resistant plant; when the exogenous gene is cowpea trypsin inhibitor gene, the process is applicable to breeding of a insect-resistant plant having a wide spectrum.

Furthermore, where antisense RNA complementary to endogenous RNA is inserted and antisense RNA is synthesized in a plant cell in large quantities, translation of endogenous RNA can be prevented; in this case, it is possible to regulate expression of a plant gene.

EXAMPLE

The present invention is described more specifically hereafter, with reference to the following examples but the invention is not to be deemed to be limited thereto.

EXAMPLE 1

Construction of BMV RNA Transcription Vector and Plant Transformation Vector

A. Preparation of cDNA of BMV RNAs 1, 2 and 3

As BMV, ATCC66 strain was used. For multiplication of the virus, barley (*Hordeum vulgare L.*, species: GOSE-SHIKOKU) was used and virus particles were purified by conventional fractional centrifugation (Okuno et al., *J. Gen. Viol.* (1978), 38:409–418). Using purified BMV, phenol extraction was prepared 3 to 4 times in the presence of bentonite and sodium dodecyl sulfate (SDS). Then, diethyl ether treatment and ethanol precipitation were performed to obtain RNA.

The resulting RNA solution was subjected to a standard separation method using low melting point agarose electrophoresis (Sambrook et al., *Molecular Cloning* (1989), 2nd, CSH Laboratory) to give RNAs 1, 2 and 3, respectively. From each of the resulting RNAs, the full length cDNA of RNAs 1, 2 and 3 were prepared using a conventional method (Ahlquist et al., *J. Mol. Biol.* (1984), 172:369–383) and cloned into a pUC vector, named pBB1, 2 and 3, respectively. Plasmids pBB1, 2 and 3 have the SnaI site at the site corresponding to the 5′ end of the full length BMV RNA and have the EcoRI site just downstream the 3′ end.

B. Construction of BMV RNA Transcription Vector and Synthesis of Infectious RNA In Vitro B-1. Construction of BMVRNA Transcription Vector (pBTF1, 2 and 3)

In order to synthesize BMV RNA in vitro, DNA-dependent RNA polymerase, T7 RNA polymerase, SP6 RNA polymerase and *E. coli* RNA polymerase, etc., which are all commercially available, were used. In this example, the in vitro BMV RNA synthesis system using T7 RNA polymerase, in which the nucleotide sequence in the promoter region and the transcription initiation site have been determined and has a high transcription efficiency (Dunn et al., *J. Mol. Viol.* (1983), 166:477–535), was used. The 5′ end structure of virus RNA has an extremely important function in replication of virus RNA or translation, etc. It is reported that when a superfluous nucleotide sequence is added to the 5′ end, the biological activity of the virus RNA is drastically reduced (Janda et al., *Virology* (1987), 158:259–262). For this reason, in order to synthesize virus RNA having the same nucleotide sequence at the 5′ end as that of wild type in vitro, transcription should be initiated precisely from the site in DNA corresponding to the 5′ end of BMV RNA.

Accordingly, in order to add the blunt end at the transcription initiation site and introduce the full length cDNA of BMV RNA, a restriction enzyme recognition site was introduced at the transcription initiation site of T7 promoter.

B-1-1. Synthesis of T7 Promoter

Using a DNA synthesizer (Applied Biosystems Co., Ltd., Model 381A), two oligonucleotides composed of 31 nucleotides: 5′pd(CTAGATGCATATAGTGAGTCGTATTAATTTA) (Seq. ID No.: 2) and 5′pd(AGCTTAAATTAATACGACTCACTATATGCAT) (Seq. ID No.: 3) were synthesized. After completion of the synthesis, the oligonucleotides were purified by high performance liquid chromatography in a conventional manner. After the oligonucleotide solution recovered was neutralized by adding 1/200 volume of 2N HCl, the mixture was added to NENSORB20 (manufactured by Du Pont Co., Ltd.) for desalting. Firstly, the column was equilibrated with 2 ml of methanol (for high performance liquid chromatography, manufactured by Nakarai Tesque Co., Ltd.), 2 ml of Solution A (0.1M Tris-HCl, 10 mM triethylamine (TEA), 1 mM$Na_2$-EDTA, pH 7.7). Next, TEA was added to the sample in a portion of 1.4 μg/ml and the resulting mixture was passed through the column for adsorption. After the column was washed with 6–9 ml of Solution A and 3 ml of ion exchange water, the oligonucleotide was eluted with 400 μl of 50% of ethanol (special grade, manufactured by Nakarai Tesque Co., Ltd.). The eluted oligonucleotide solution was evaporated to dryness under reduced pressure using an evaporator.

The residue was dissolved in ion exchange water to prepare a 1 μg/ml oligonucleotide solution.

The 5′ and 3′ ends of these synthetic oligonucleotides were phosphorylated. More specifically, a reaction solution containing 1 μl of each oligonucleotide (1 μg/ml), 20 μl of 10 mMATP, 20 μl of 10× kinase solution (500 mM Tris-HCl, pH 7.5, 100 mM $MgCl_2$, 100 mM dithiothreitol (DTT)), 4 μl of T4 polynucleotide kinase (4 units/μl, manufactured by Takara Shuzo Co., Ltd.) and 155 μl of ion exchange water was reacted at 37° C. for an hour to phosphorylate the oligonucleotide. After the reaction, the enzyme was inactivated by a heat treatment at 65° C. for 10 minutes. The reaction solution was treated twice with phenol, once with phenol/chloroform, once with chloroform and 3 times with diethyl ether. Thereafter, the reaction solution was allowed to stand for 30 to 40 minutes under reduced pressure and diethyl ether present in the reaction solution was completely removed. The reaction solution was added to a NENSORB20 column and the phosphorylated oligonucleotides were purified as described above. Thereafter, the solution was evaporated to dryness and the residue was dissolved in distilled water at a concentration of 50 ng/ml. The solution was then subjected to the following procedure.

These synthetic oligonucleotides were annealed to synthesize a T7 promoter. The sequence of this promoter has a HindIII site at the 5′ end and a XbaI site as being staggered, in addition to the consensus sequence of the T7 promoter, and further has a NsiI site at the (+4) position from the transcription initiation site.

B-1-2. Introduction of the Full Length cDNA of BMV RNA into Transcription Vector pUCT (FIG. 5)

The synthesized T7 promoter was introduced into pUC19 at the HindIII/XbaI site to construct transcription vector pUCT. pUCT was treated with NsiI and T4 DNA polymerase thereby to remove the nucleotides of T7 promoter up to the (+1) position and form a blunt end at the (−1) position. The SnaBI/EcoRI fragment containing the full length cDNA of respective BMV RNAs of pBB1, pBB2 and pBB3 was ligated with a large fragment of pUCT which had been treated with NsiI and T4 polymerase followed by treatment with EcoRI to construct transcription vectors pBTF1, pBTF2 and pBTF3 of BMVRNAs 1, 2 and 3, respectively.

B-2. Synthesis of Infectious RNA In Vitro (FIG. 5)

The plasmid DNAs of transcription vectors pBTF1, pBTF2 and pBTF3, in which the respective full length cDNA of RNAs 1, 2 and 3 had been introduced immediately downstream the transcription initiation site of T7 promoter and the EcoRI site was present immediately downstream the full length cDNA of RNA, were purified by the cesium chloride centrifugation method (Sambrook et al., *Molecular Cloning (*1989), 2nd, CSH Laboratory). After 3 μg of each of the purified DNA was cleaved with EcoRI, treatment with phenol/chloroform was performed followed by ethanol precipitation using 20 μg tRNA as a carrier. After 16.8 μl of distilled water, 10 μl of 5× transcription buffer (200 mM Tris-HCl (pH 7.5), 30 mM $MgCl_2$, 10 mM spermidine, 50 mM NaCl), 5 μl of 100 mM DTT, 1.8 μl of DNase/RNase free bovine serum albumin (2.8 mg/ml), 2.5 μl of RNasin (40 units/ml), 2.5 μl of 10 mM ATP, 2.5 μl of 10 mM UTP, 2.5 μl of 10 mM CTP, 0.4 μl of 10 mM GTP and 5 μl of 5 mM cap analog (m7GpppG) were added to the resulting precipitates, the mixture was gently mixed. Then 1 μl of T7 polymerase was added, and reacted at 37° C. One hour later, an additional 2 μl of 10 mM GTP and 1 μl of T7 polymerase were added, and the mixture was reacted at 37° C. for an hour. Thereafter, 1.3 μl of DNase (1 unit/ml) was added and the mixture was reacted at 37° C. for an hour to decompose the template DNA. The reaction solution was treated once each with phenol/chloroform and with chloroform followed by ethanol precipitation using 20 μg of tRNA as a carrier. The precipitates were suspended in 10 μl of distilled water.

The respective transcription products of the cDNA of BMV RNAs 1, 2 and 3 synthesized in vitro by the process described above were mixed with each other and an equal volume of 2× inoculation buffer (100 mM Tris-phosphate (pH 8.0), 500 mM NaCl, 10 mM EDTA, 1% (W/V) bentonite) was added to the mixture. The thus obtained solution was used as an inoculation solution. Carborundum (600 mesh) was sprinkled over barley leaf, which was a systemic infection host, and 5 to 10 μl of inoculation solution drops were spread and inoculated on the leaf. Immediately after inoculation, carborundum on the leaf was washed off with tap water. For about 2 weeks, the barley leaf was grown in a growth chamber (8,000 LUX) at 25° C., where the leaf expressed systemic symptoms. This thus confirmed that the transcription products of transcription vectors pBTF1, 2 and 3 were infectious.

C. Construction of Plant Transformation Vector

C-1. Introduction of Restriction Enzyme Recognition Site into CaMV35S Promoter at Transcription Initiation Site Introduction of full length cDNA of BMV RNA between the promoter and terminator recognized by a DNA-dependent RNA polymerase present in a plant cell. As the promoter, CaMV35S promoter was used, taking into account that its transcription amount was large and the transcription initiation site and the nucleotide sequence in the promoter region were determined. Furthermore, it has been shown that BMV RNA mutant having a superfluous nucleotide sequence of 7 bases at the 5' end has no infectious ability (Janda et al., *Virology (*1987), 158:259–262). Therefore, in order to impart multiplication ability to the nuclear transcription product of the full length cDNA of BMV RNA inserted in a plant cell, it was necessary to accurately coincide the transcription initiation site of the DNA with the site in the cDNA corresponding to the 5' end of BMV RNA. Thus, for the purpose of introducing the full length cDNA of BMV RNA right downstream the transcription initiation site, the recognition site of the restriction enzyme was introduced into CaMV35S promoter at the transcription initiation site by site-directed mutagenesis.

C-2. Site-Directed Mutagenesis (FIG. 3)

Plasmid pCAM35 which had the 35S promoter region (7016–7434) of CaMV CM1841 strain, accessed in the Faculty of Plant Disease, Department of Agricultural Science, Kyoto University, immediately upstream pUC18-derived polylinker sequence and 35S terminator region (7436–7606) of CaMV CM1841, was used. In order to prepare single-stranded DNA in the CaMV35S promoter region, the PstI/EcoRI fragment of pCAM35 was introduced into pUC18 at the PstI/EcoRI site to construct pCAM35EP. *E. coli* MV1184 strain was transformed by pCAM35EP and single stranded DNA was prepared utilizing helper phage M13K07.

In order to introduce the StuI site into the transcription initiation site, an oligonucleotide of 25 bases: 5'pd(GTAGGCCTCTCCAAATGAAATGAAC) (Seq. ID. No.: 4) complementary to the transcription initiation site of the prepared single-stranded DNA, except for 3 mismatches, was synthesized and prepared by the procedure described in B-1-1 above. In a 1.5 ml Eppendorf tube were charged 1 μl of single-stranded DNA (20 μg/μl), 1 μl of synthetic oligonucleotide (2 μg/μl), 20 μl of 10× annealing buffer (200 mM Tris-HCl (pH 7.5), 100 mM $MgCl_2$, 500 mM NaCl, 10 mM DTT) and 178 μl of distilled water. After treating at 62° C. for 15 minutes, the mixture was slowly cooled at room temperature for 7 minutes to anneal the synthetic oligonucleotide to single-stranded DNA. After the annealing, 40 μl of Klenow buffer (100 mM Tris-HCl (pH 7.5), 50 mM $MgCl_2$, 50 mM DTT), 20 μl of dNTP solution (2 mM each of dATP, dCTP, dGTP, dTTP), 10 μl of Klenow fragment (4 units/ml) and 130 μl of distilled water were added, the mixture was subjected to an enzyme reaction at 22° C. for 5 hours to synthesize a complementary DNA strand using the synthetic oligonucleotide as a primer. After the reaction, the reaction solution was treated with phenol, with phenol/chloroform and with diethyl ether and then precipitated with ethanol to produce double-stranded DNA precipitates. After this double-stranded DNA was cleaved with PvuII, the cleavage product was treated with phenol/chloroform and then precipitated with ethanol. The resulting precipitates were mixed with 1.5 μl of loading buffer (0.89M Tris-borate, 2 mM EDTA, 0.2% (W/V) bromophenol blue, 0.2% (W/V) xylene cyanol) and 432 μl of formaldehyde. After treatment at 95° C. for 5 minutes, the mixture was quenched with ice water. This sample was loaded on 3.5% polyacrylamide-7M urea gel (15 cm×15 cm, thickness of 2 mm, slot width of 1 cm), which was subjected to electrophoresis at 200 V for 2 hours. Thus, single-stranded DNA synthesized using the primer was isolated. After staining with ethydium bromide (0.5 μg/ml), the gel was washed 3 times with about 30 ml of ion exchange water to remove an excess of ethydium bromide and urea. By exposing such to UV light, the desired band was excised and the gel was passed through a 1 ml syringe (Terumo Co., Ltd.) to form gel pieces. The gel pieces were added to 7 ml of elution buffer (500 mM ammonium acetate, 10 mM magnesium acetate, 1 mM EDTA, 0.1% SDS). The mixture was allowed to stand at 37° C. overnight. After centrifugation at 5000×g for 3 minutes, the supernatant was treated twice with phenol, once with phenol/chloroform, once with chloroform and 3 times with diethyl ether. After the solution was concentrated 4-fold with 2-butanol, a 2-fold volume of ethanol and 10 μl of tRNA (2 mg/ml) was added to the concentrate. By ethanol precipitation, a single-stranded DNA precipitate were obtained and the precipitate was dissolved in 30 μl of distilled water. By mixing together 5 μl of the recovered single-stranded DNA (0.2 μg/μl), 1.5 μl of M13 reverse primer (50 ng/μl, M13 primer RV, manufactured by Takara Shuzo Co., Ltd.), 1 μl of annealing buffer (100 mM Tris-HCl (pH 7.5), 100 mM $MgCl_2$, 500 mM NaCl), 1.5 μl of TE buffer (10 mM Tris-HCl (pH 8.0), 1 mM EDTA) and 1 μl of Klenow fragment (4 units/μl), a double-stranded DNA fragment was synthesized and the StuI site was introduced at the transcription initiation site. The synthesized fragment of the 35S promoter region was cleaved with EcoRI and the cleavage product was introduced into pUC18 at the EcoRI/SmaI site to construct pCaP35 containing the modified 35S promoter region. By cleaving pCaP35 with StuI, the transcription initiation site can be rendered a blunt end and the full length DNA of BMV RNA can be introduced immediately downstream the transcription initiation site.

C-3. Construction of Plant Transformation Vector (pBICBR series) (FIG. 6)

By inserting the full length cDNA of BMV RNA in a genome of a plant, a vector was constructed to create a transformed plant in which the transcription product has the ability for translation and multiplication as in wild type virus RNA.

CaMV35S promoter, pUC18-derived polylinker site and CaMV terminator were introduced into an Agrobacterium binary vector pBIN19 (Bevaney et al., *Nucl. Acids Res.* (1984), 12:8711–8721) for plant transformation at the EcoRI/HindIII site. The resulting plasmid was designated pBIC35. After pBIC35 was cleaved with EcoRI, the digestion product was blunt ended using a T4 DNA polymerase treatment and SalI linker was added. After cleavage with SalI, self ligation was performed to construct pBICT(-E) with CaMV35S promoter deleted. Then, after further adding EcoRI linker, pBICT(-E) cleaved with SmaI was subjected to self ligation to construct pBICTE with the EcoRI site modified from the SmaI site. On the other hand, pCaP35 containing CaMV35S promoter modified by introducing the StuI site into CaMV35S promoter at the transcription initiation site by site-directed mutagenesis was cleaved with EcoRI. Then, both ends were blunt ended using a T4 DNA polymerase treatment and SalI linker was added to both ends. On cleavage with SalI and BamHI, DNA fragment containing the modified CaMV35S promoter was obtained. The fragment was introduced into pBICTE at the SalI and BamHI site to construct pBICP35.

Next, the SnaBI/EcoRI fragments of pBB1, pBB2 and pBB3 containing the full length cDNA fragment of BMV RNAs 1, 2 and 3 were introduced into pBICP35 at the StuI/EcoRI site, respectively, to construct plant transformation vector pBICBR1, 2 and 3, respectively (FIG. 6).

C-4. Construction of Plant Transformation Vector (pBICBMR series) (FIGS. 7–9)

By introducing the DNA, in which the portion corresponding to the 3′ end of BMV RNA was deleted, into the genome of a plant cell, a vector was constructed to create a transformant in which the transcription initiation product synthesized has translation ability but does not have multiplication ability as in wild type virus RNA.

After pBB1 containing the full length cDNA of BMVRNA1 was cleaved with XhoI, the cleavage product was treated with T4 polymerase to render both ends blunt. Then, EcoRI linker was added thereto. After further cleavage with EcoRI, self ligation was performed. As a result, pBBI(-3) with a deletion of about 200 bases downstream XhoI in the DNA corresponding to the 3′ non-translated region of RNA1 was obtained. The SnaBI/EcoRI fragment containing RNA1cDNA of pBBi(-3) was introduced into pBICCP35 at the StuI/EcoRI site to construct plant transformation vector pBICBMR1 (FIG. 7).

After pBB2 containing the full length cDNA of BMVRNA2 was cleaved with PstI and HindIII, the DNA fragment was introduced into pUC18 at the PstI/HindIII site to obtain pBB2(-H) containing cDNA deleted of the 3′ non-translated region of RNA2. After pBB2(-H) was cleaved with HindIII, the cleavage product was treated with T4 DNA polymerase to render both ends blunt. Then, EcoRI linker was added thereto. After further cleaving with EcoRI, self ligation was performed. As a result, pBB2(-3) with a deletion of about 200 bases downstream HindIII in the cDNA corresponding to the 3′ non-translated region of RNA2 was obtained. The SnaBI/EcoRI fragment containing RNA2cDNA of pBB2(-3) was introduced into pBICP35 at the StUI/EcoRI site to construct plant transformation vector pBICBMR2 (FIG. 8).

After pBB3 containing the full length cDNA of BMVRNA3 was cleaved with PstI and HindIII, the DNA fragment was introduced into pUC18 at the PstI/HindIII site to obtain pBB3(-H) containing cDNA with the 3′ non-translated region of RNA3 deleted. After pBB3(-H) was cleaved with HindIII, the cleavage product was treated with T4 DNA polymerase to render both ends blunt. Then, EcoRI linker was added thereto. After further cleavage with EcoRI, self ligation was performed. As a result, pBB3(-3) with a deletion of about 200 bases downstream HindIII in the cDNA corresponding to the 3′ non-translated region of RNA3 was obtained. The SnaBI/EcoRI fragment containing RNA3cDNA of pBB3(-3) was introduced into pBICP35 at the StuI/EcoRI site to construct plant transformation vector pBICBMR3 (FIG. 9).

EXAMPLE 2

Expression of the Respective BMV Genes in Transformed Plant Cell

A. Introduction of Plant Transformation vector into *A. tumefaciens*

On one NB agar medium (0.8% Nutrient Broth, 1.5% Bacto Agar), *E. coli* DH5α strain (harboring pBICBR or pBICBMR vector), *E. coli* HB101 strain (harboring helper plasmid pRK2013) and *A. tumefaciens* LBA4404 strain (harboring Ti plasmid with T-DNA region deleted) were inoculated, respectively followed by incubation at 30° C. for 2 days. After the incubation, 3 kinds of bacteria were mixed with a sterilized platinum loop followed by incubation at 30° C. for 2 days additionally. The mix-cultured bacteria was streaked on AB agar medium (Table 1) containing 50 μg/ml of kanamycin and cultured at 30° C. for 2 days to obtain a single colony. This colony is *A. tumefaciens* LBA4404 strain harboring a transformation vector.

B. Inoculation of Tobacco with *A. Tumefaciens* and Selection of Transformants

As tobacco for inoculation (*Nicotiana tabacum* cv. Petit Habana SR1), a sterile plant derived from a sterilized seed was used. About 100 μl of tobacco seed in a 1.5 ml Eppendorf tube was washed with 1 ml of 70% ethanol. Next, 1.5 ml of 20% antiformin was added to the tobacco seed. While stirring for a second every other 4 minutes, the mixture was allowed to stand at room temperature for 20 minutes to sterilize the seed. After the sterilization, the seed was washed 3–4 times with sterile water and inoculated onto LS1 medium (Table 2) in a plastic Petri dish (Seibu Co., Ltd., 90 mm in diameter, 20 mm in depth) followed by growth at 26° C. under 8,000 LUX. The young plant, after growth to about 1 cm, was transplanted to a biopot (Nippon Medical Chemical Machine Co., Ltd.) with LS8 medium (Table 2). The plant after growth to a height of about 10 cm was used for *A. tumefaciens* inoculation.

*A. tumefaciens* harboring the transformation vector was cultured by shaking (120 rpm) at 30° C. for 2 days in AB liquid medium containing 50 μg/ml of kanamycin.

The operations subsequent thereto were all performed aseptically. The tobacco leaf grown aseptically was cut into 1 cm×1 cm and immersed in the above described culture broth of *A. tumefaciens* for a minute. This leaf piece was placed on a paper towel, which had been previously sterilized, to remove excess bacterial solution. This leaf piece was placed on LS1 medium (Table 2), with the back surface turned up. After incubation at 26° C. for 48 to 72 hours, the leaf piece was transferred onto LS1 liquid medium containing 500 μg/ml of carbenicillin and cultured at 26° C. for 2 days under 700 LUX to fully remove *A. tumefaciens*. After the incubation, this leaf piece was placed on a paper towel, which had been previously sterilized, to remove LS1 liquid medium. Then the leaf piece was transferred onto LS4 medium (Table 2) containing 150 μg/ml of kanamycin and 100 μg/ml of carbenicillin, and cultured at 26° C. for about 2 to 3 weeks under 8,000 LUX. A sprouted shoot 5–10 mm tall was cut out of a callus with a sterilized surgical knife and transferred onto MSR medium containing 100 μg/ml of kanamycin and 150 μg/ml of carbenicillin (LS plate medium containing 525 μg/ml of naphthalene acetic acid and 100 μg/ml of 6-benzyladenine, using Gelangum instead of agar). Two weeks later, the young plant had grown to about 5 cm overall and was transplanted to a flowerpot having a diameter of 12 cm and the plant was covered with a transparent plastic box for conditioning the plant for several days. Then, the plant was grown in a growth chamber.

Kanamycin-resistant tobacco transformed by transformation vectors pBICBR1, pBICBR2 and pBICBR3 were named BR1, BR2 and BR3, respectively, and kanamycin-resistant tobacco transformed by transformation vectors pBICBMR1, pBICBMR2 and pBICBMR3 were named BMR1, BMR2 and BMR3, respectively.

C. Analysis on Expression of Each Gene of BMV Inserted into Tobacco Genome

For determinating whether each gene of BMV inserted is expressed in the transformed plant showing kanamycin resistance, analysis of the expression of the introduced 1a gene was made by inoculating a protoplast prepared from the transformed tobacco BR1 or BMR1 with a mixture of RNAs 2 and 3, and analysis of the expression of the 2a gene was made by inoculating protoplast prepared from the transformed tobacco BR2 or BMR2 with a mixture of RNAs 1 and 3. RNAs 1, 2 and 3 were synthesized in vitro from pBTF1, 2 and 3 by the process described in Example 1B.

In the cell in which virus replicase, 1a and 2a proteins, are expressed, it is believed that RNA4, which is mRNA of coat protein, would be synthesized from the inoculated RNA3 and coat protein of BMV would accumulate in the cell. It is considered that coat protein would not be directly translated from RNA3 but would be translated by replicase via RNA4 synthesized from (−)-stranded RNA3 (Miller et al., *Nature* (1985), 313:68–70); by detecting the production of coat protein, production of replicase, or 1a and 2a proteins which are subunits of the enzyme can be indirectly detected. Thus, analysis on production of coat protein was made by Western blotting using anti-BMV antibody.

C-1. Preparation of Protoplast

The 4th to 5th leaves of a tobacco plant at 15–20 cm length stage were used for preparation of protoplasts. The back epidermis of the cut tobacco leaf was peeled apart and immersed in 0.5M mannitol solution (pH adjusted to 5.6–5.8 with KOH) containing 1% Cellulase Onozuka R-10 (Kinki Yakult Co., Ltd.) and 0.05% MACEROZYME R-10 (Kinki Yakult Co., Ltd.), in a flask of a volume of 100 ml. While the flask was gently shaken every other 15 minutes, the leaf was treated at 26° C. for 2 hours. The undecomposed tissue present in the resulting protoplast suspension was filtered through a 4- to 6-layered gauze and transferred to a 50 ml glass centrifuging tube. The protoplast was collected by centrifugation at 100×g for 2 minutes. Centrifugal washing was repeated twice further with 0.5M mannitol solution.

C-2. Inoculation of Tobacco Protoplast with BMV BNA

A protoplast suspension in 0.5M mannitol was transferred to 4 to 6 polypropylene culture tubes of a volume of 10 ml (Nissui Pharmaceutical Co., Ltd., #06480). The protoplast was collected by centrifugation at 100×g for 2 minutes and the supernatant was removed. To the protoplast was added 0.7 ml of T solution (0.5 M mannitol, 40 mM $CaCl_2$) containing 2–10 μg of BMV RNA and 10 μg of tRNA. After thoroughly mixing them, 0.7 ml of PEG solution (40% PEG 4000, 0.5M mannitol, 40 mM $CaCl_2$) was immediately added to the mixture. Each tube was inverted to gently mix and shaken on ice for 30 minutes at a low speed. Thereafter, about 8 ml of T solution was added to the mixture. Each tube was inverted to gently mix and settled on ice for 30 minutes. After the protoplast was collected by centrifugation at 100×g for 2 minutes, centrifugal washing was repeated 3 times with High-pH High-$Ca^{2+}$ buffer (0.7M mannitol, 50 mM $CaCl_2$, 50 mM glycine, pH 8.5) to remove PEG and non-adsorbed RNA. The protoplast was suspended in 3 ml of 0.7 i medium (0.2 mM $KH_2PO_4$, 1 mM $KNO_3$, 1 mM $MgSO_4 \cdot 7H_2O$, 10 mM $CaCl_2 \cdot 2H_2O$, 0.1 μM KI, 0.01 μM $CuSO_4 \cdot 5H_2O$, 0.7M mannitol, 2500 units/ml mycostatin, 200 μg/ml chloramphenicol, pH 6.5) followed by inoculation at 26° C. for 48 hours.

C-3. Preparation of Antibody and Western Blotting Analysis

Anti-BMV sera were purified using the ammonium sulfate method to obtain a γ-globulin fraction. Acetone powder was prepared from the tobacco protoplast, and reacted with the purified anti-BMV antibody described above, whereby, the antibody non-specifically binding to the plant component was removed. After the protein extracted from the protoplast inoculated with BMV RNA was subjected to SDS-polyacrylamide gel electrophoresis, the isolated protein was electrically transferred onto a membrane (Immobilon-P, manufactured by Millipore Co., Ltd.) by the method of Towbin et al. (Towbin et al., *Pro. Natl. Acad. Sci. USA* (1979), 76:4350–4354). After the transfer, detection of BMV coat protein was made using the coloring reaction on NTB-BCIP as a substrate, with the purified anti-BMV antibody diluted to 1/400 as a primary antibody and anti-rabbit IgG-goat IgG labeled with alkaline phosphatase as a secondary antibody.

C-4. Analysis of Introduced Gene Product in BR1 and 2 Plant Cells

The protoplast prepared from a BR1 plant was inoculated with RNA 2+3 synthesized in vitro. Further as a positive control, a protoplast was inoculated with RNA 1+2+3. Forty-eight hours after the inoculation, the relative evaluation of coat protein synthesized in the transformed plant was made using Western blotting analysis. The evaluation was conducted as follows, when the average value of the expression degree of coat protein gene in the positive control was set at 100%.

| | Average Value for Expression of Coat Protein |
|---|---|
| BR1 Plant Inoculated with RNA 1 + 2 + 3 | 100 |
| BR1 Plant Inoculated with Mock | 0 |
| BR1 Plant Inoculated with RNA 1 + 3 | 0 |
| BR1 Plant Inoculated with RNA 2 + 3 | 110 |

In the BR1 plant inoculated with 2+3, the coat protein was detected at a level similar to that in the BR1 plant inoculated with 1+2+3. It was thus confirmed that the complete la protein was produced in all cells of the BR1 plant.

Also the protoplast prepared from BR2 plant was inoculated and coat protein was detected as follows.

| | Average Value for Expression of Coat Protein |
|---|---|
| BR2 Plant Inoculated with RNA 1 + 2 + 3 | 100 |
| BR2 Plant Inoculated with Mock | 0 |

-continued

| | Average Value for Expression of Coat Protein |
|---|---|
| BR2 Plant Inoculated with RNA 2 + 3 | 0 |
| BR1 Plant Inoculated with RNA 1 + 3 | 98 |

In the case where RNA 1+3 was inoculated without inoculating RNA 1+2+3, coat protein was produced in the protoplast at a level similar to that of the group inoculated with RNA 1+2+3. It was thus confirmed that complete 2a protein was produced in all cells of the BR2 plant.

C-5. Analysis of the Introduced Gene Product in BMR1 and 2 Plant Cells

The protoplast prepared from BMR1 and 2 was inoculated with RNA synthesized in vitro. Forty-eight hours after the inoculation, coat protein in the protoplast was detected by Western blotting. The results demonstrate that also where the protoplast prepared from BMR1, in which cDNA of RNA1 using pBICBMR vector with a deletion only at the 3′ non-translated region was inoculated with RNA 2+3, coat protein was detected on a level similar to that in the case inoculated with RNA 1+2+3. Also where BMR2 was inoculated with RNA 1+3, coat protein was detected.

| | Average Value for Expression of Coat Protein |
|---|---|
| BMR1 Plant Inoculated with RNA 1 + 2 + 3 | 100 |
| BMR1 Plant Inoculated with Mock | 0 |
| BMR1 Plant Inoculated with RNA 2 + 3 | 105 |
| BMR1 Plant Inoculated with RNA 1 + 3 | 0 |
| BMR2 Plant Inoculated with RNA 1 + 2 + 3 | 100 |
| BMR2 Plant Inoculated with Mock | 0 |
| BMR2 Plant Inoculated with RNA 2 + 3 | 0 |
| BMR2 Plant Inoculated with RNA 1 + 3 | 90 |

In BMR1 or BMR2, it was shown that all 1a proteins or 2a proteins necessary for replication of virus depend on transcription and translation from the plant genome, since the transcription product of cDNA of RNA1 or RNA2 introduced into the genome of plant lacks replication ability. It has also been demonstrated that each gene of the virus could be made independent of the complicated control mechanism of the virus but rather, dependent on the mechanism of transcription and translation of the plant.

C-6. Preparation of Tobacco Plant Which Produces BMV Replicase

A crossing between BR1 plant and BR2 plant, and BMR1 plant and BMR2 plant was performed respectively. The crossing was performed by picking anthers of the pollen parent BR1 plant which was in bloom, fertilizing a stamen of the BMR2 plant which has been de-antherized, and the seed recovered 4 weeks later. The crossing between BMR1 plant and BMR2 plant was performed in the same way. The seed obtained was germinated on LS1 medium containing kanamycin (50 μg/ml), and kanamycin-resistant tobacco was selected. The coat protein can be produced by inoculation of RNA3 on the protoplast, because a plant in which both the cDNA of RNA1 and RNA2 are inserted into the genome produces 1a and 2a proteins. Thus, the tobacco plants which produced the coat protein was selected from kanamycin-resistant plants using the same method as in the Example 2C-4 and 5. The F1 plants of the BR1 plant and the BR2 plant obtained by the above-mentioned crossing method were designated BMR(1+2). These are plants in which both the cDNA of RNA1 and RNA2 are inserted into the genome, and which produce 1a and 2a proteins.

Next, in order to obtain pure diploid BR(1+2) and BMR(1+2) plants, according to the Imamura et al. method (Imamura et al., *Plant Cell Physio* 1. (1982), 23:713–716), the anther culture is performed, when the second leaf of the young haploid plant obtained appears, 0.2% of colchicine was applied to the top of the bud. The plant which appears to a diploid plant is elected, and individual which produced the coat protein was elected according to the same method as in the Example 2C-4 and 5, to obtain pure diploid.

The pure diploid obtained from BR(1+2) and BMR(1+2) plants were designated as BRP(1+2) and BMRP(1+2), respectively.

EXAMPLE 3

Production of IFN

BMV ACTT66 strain was used as a RNA plant virus and the human-derived gamma-interferon (IFN) gene was used as a desired exogenous gene. A characteristic of the IFN gene is that it is an animal-derived gene and a sugar chain is added after translation. Furthermore, the N-terminal and C-terminal are processed. The gene of interferon has about 500 bp, and encodes a protein composed of about 170 amino acids. When this gene is expressed in an animal cell, three species are detected due to addition of a sugar chain and the processing of both termini (Gray et al., *Nature* (1982), 295:503–505).

A. Construction of BMV-IFN Chimera RNA Transcription Vector (FIG. 10–15)

For construction of BMV-IFN chimera RNA transcription vector, plasmids pBTF1, 2 and 3 in which full length cDNA of BMV RNA1, 2 and 3 are inserted downstream from the T7 promoter were used (FIG. 5). In order to replace virus genes which encode 1a, 2a and two kinds of coat proteins (CP1 and 2) with the IFN gene, an NsiI site was introduced at the site of the initiation codon of BMVcDNA and IFN gene by the Kunkel et al. method (Kunkel et al., *Methods in Enzymology* (1987), 154:367–382) (FIG. 4). In order to conduct site-directed mutagenesis, the following oligonucleotides were synthesized according to Example 1B-1-1. For 1a protein in pBTF1, 5′pd(GTTTTTCACCAACAAAATGCATAGTTCTATCGATTTGC); (Seq. ID. No.: 5) for 2a protein in pBTF2, 5′pd(CACCAAGATGCATTCGAAAACC); (Seq. ID. No.: 6) for 3a protein in pBTF3, 5′pd(GTTCCCGATGCATAACATAGTTT); (Seq. ID. No.: 7) for CP1 protein in pBTF3, 5′pd(GTATTTAATGCATACTTCAGGAAC); (Seq. ID. No.: 8) for CP2 protein in pBTF3, 5′pd(TGGTAAGATGCACGCGCGCAGC); (Seq. ID. No.: 9) and for the IFN gene (obtained from Daiichi Seiyaku Co., Ltd.) pMKC, 5′pd(TCTCTCGGAATGCATGCATGAAATATAC) (Seq. ID. No.: 10) were used respectively. Using these, pBTF1a, pBTF2a, pBTF3a, pBTFpCP1, pBTFpCP2 and pUCpIFN(Nsi) were constructed respectively. Further, SacI site was introduced immediately downstream of stop codon in pUCpIFN(-Nsi), using the oligonucleotide 5′pd(CCCAGTAATGGAGCTCCTGCCTGC) (Seq. ID. No.: 11) to construct pUCIFN(Nsi). pBTF3a was cleaved with ClaI and StuI, and then it was rendered blunt ended by T4 DNA polymerase treatment and SacI linker was added. Further, after cleaving with SacI, self ligation was performed. The subgenomic RNA promoter was deleted from the plasmid pBTF3a1 obtained and its ClaI site was replaced with SacI.

After cleaving pBTF3a with SacI and StuI, self ligation was performed, and then blunt ended by using a T4 DNA polymerase treatment to perform self ligation. The NsiI site was deleted from the plasmid pBTF3a2 obtained. After cleaving pBTF3a2 with ClaI, it was rendered blunt ended by using T4 DNA polymerase, and SacI linker was added. Further, after cleaving with SacI, self ligation was performed. In the plasmid pBTF3a3 obtained, its ClaI site was replaced with SacI. After cleaving pBTFp CP1 and pBTFp CP2 with StuI, SacI linker was added. Further, after cleaving with SacI, self ligation was performed. In the plasmid pBTFCP1 and pBTFCP2 obtained, StuI was replaced with SacI. Ligation of a big fragment (fragment containing plasmid) obtained by cleaving pBTF2a, pBTF3al, pBTF3a3, pBTFCP1 and pBTFCP2 with NsiI and SacI, and IFN gene fragment obtained by cleaving pUCIFN(Nsi) with NsiI and SacI were performed to construct pBTF2apIFN, pBTF3alpIFN, pBTF3a3pIFN, pBTFCP1pIFN and pBTFCP2pIFN.

pBTF1a was cleaved with NruI (blunt end cleaved) and NsiI. The big fragment obtained and the IFN gene fragment obtained by cleaving pUCIFN(Nsi) with SacI, followed by treatment with T4DNA polymerase to perform blunt ending, and then cleavage with NsiI were ligated to construct pBTF1apIFN.

After pBTF1apIFN, pBTF2apIFN, pBTF3a1pIFN, pBTF3a3pIFN, pBTFCP1pIFN and pBTFCP2pIFN were cleaved with NsiI, they were blunt ended by T4 DNA polymerase, and self ligation was performed to construct pBTF1aIFN, pBTF2aIFN, pBTF3a1IFN, pBTF3a3IFN, pBTFCP1IFN and pBTFCP2IFN.

The ligation of the big fragment by cleaving pBTF3a3IFN with BglII and EcoRI and the small fragment by cleaving pBTF3 with BglII and EcoRI was performed to construct pBTF3a4IFN.

After pBTF3a4 was cleaved with BssHI, it was blunt ended using T4 DNA polymerase, and self ligation was performed. In the pBTF3a4IFN thus obtained, a frame shift was introduced in the BMV coat protein gene.

B. Synthesis of Infectious RNA In Vitro and Inoculation on Tobacco Protoplast

Synthesis of infectious RNA in vitro was performed from plasmids pBTF1, 2 and 3 which transcribed the respective full length cDNA of BMVRNA1, 2 and 3, or plasmid pBTF1aIFN, pBTF2aIFN, pBTF3a1IFN, pBTF3a4IFN, pBTF3a5IFN, pBTFCP1IFN and pBTFCP2IFN which transcribed BMV-IFN chimera RNA. As a result, BMVRNA 1, 2 and 3 and 7 kinds of BMV-IFN chimera RNA were obtained. The BMV-IFN chimera RNAs obtained were designated F1aIFN, F2aIFN, F3a1IFN, F3a4IFN, F3a5IFN, FCP1IFN and FCP2IFN (FIG. 16), respectively.

Each of BMV-IFN chimera RNA and wild type BMVRNA3 as a control were mixed with RNA1 and 2 respectively, and a tobacco protoplast inoculated therewith using the method in Example 2C.

C. Replication of BMV-IFN Chimera RNA

Each of BMV-IFN chimera RNA and wild type BMVRNA3 as a control were mixed with RNA1 and 2 respectively, and a tobacco protoplast was inoculated with the mixture. After 48 hours, entire RNA was prepared from the tobacco protoplast, Northern blotting was performed using the 3′ end sequence which is common to entire BMVRNA. Replication of chimera RNA and synthesis of subgenomic RNA was evaluated by Northern blotting.

The results obtained were as follows when replication of chimera RNA and synthesis of subgenomic RNA in the wild strain BMVRNA3 which was a positive control was set at 100%.

| | Replication of Chimera RNA | Synthesis of Subgenomic RNA |
|---|---|---|
| F1aIFN | 1 | — |
| F2aIFN | 1 | — |
| F3a1IFN | 1 | — |
| F3a4IFN | 60 | 60 |
| F3a5IFN | 80 | 80 |
| FCPLIFN | 40 | 20 |
| FCP2IFN | 40 | 20 |
| RNA3 | 100 | 100 |

As a result, only F3a4IFN, F3a5IFN, FCP1IFN and FCP2IFN were replicated, and subgenomic RNA was also synthesized. The subgenomic RNA synthesized from FCP1IFN or FCP2IFN corresponded to 20% of RNA4 synthesized from wild strain RNA3. On the otherhand, there was not any large difference between the amounts of RNA transcribed from F3a4IFN or F3a5IFN and the amounts of RNA4 transcribed from the wild strain RNA3. Further, when the amounts of entire RNA in the protoplast was measured and compared with the amounts of subgenomic RNA synthesized from FCP2IFN, the amounts of RNA synthesized from FCP2IFN was about 1% of the entire RNA.

D. Analysis of Production Amounts of IFN in Protoplast Inoculated With BMV-IFN Chimera RNA Each of BMV-IFN chimera RNA and wild type BMVRNA3 as a control described above were mixed with RNA1 and 2 respectively, and a tobacco protoplast was inoculated. After 48 hours, entire protein was extracted from the tobacco protoplast, the amounts of IFN produced in each test were measured by the Western blotting analysis using anti-IFN antibody. The results were as follows, when the average amounts of IFN produced in the experimental zone using FCP2IFN in which the highest IFN production amounts were obtained was set at 100%.

| | Amounts of IFN Protein |
|---|---|
| F1aIFN | 0 |
| F2aIFN | 0 |
| F3a1IFN | 0 |
| F3a4IFN | 15 |
| F3a5IFN | 15 |
| FCP1IFN | 15 |
| FCP2IFN | 100 |

As a result, only in the experimental zone using F3a4IFN, F3a5IFN, FCP1IFN and FCP2IFN, three IFN species which seemed to be due to sugar addition and processing of both termini were produced. Of these, the highest level of IFN production was observed in the zone using FCP2IFN. The IFN production amounts was set at 100% and the relative production amounts in the other experimental zones were calculated. In the zones using F3a4IFN, F3a5IFN and FCP1IFN, about 15% of the IFN in FCP2IFN was produced. On the otherhand, from the fluoroimmuno-staining method, it was determined that in the zones using FCP1IFN, IFN was produced at about 10% of the protoplast. When the absolute amount of IFN was measured for comparison with the control zone using a commercially available IFN (JCR Co.), the amount was about 50 pg, which corresponded to 5% of the amount of the total protein. That is, the amounts of IFN were produced at a level which was as good as that of coat protein. From the above results, it was determined that when on or after the second initiation codon was replaced with IFN gene, the production ability of the protein were more than 6 times, in comparison with the case of the usual method where on or after the first translation initiation codon was replaced.

E. Construction of Vectors for Transcription of Wild Type RNA4 or BMV-IFN Chimera RNA4 in Which CP2 Gene Is Replaced with IFN Gene and Transcription of RNA In Vitro (FIG. 17)

As described above, it is not clear in FCP2IFN whether the translation started at the first translation initiation codon or at the second translation initiation codon, since the translation products of IFN in vitro were recognized as three species as a result of modification after the translation. Thus, in order to exclude the influence of the modification after the translation, use of a protein translation system in vitro was attempted. Further, BMV RNA3 has no coat protein translation efficiency and the coat protein is translated from RNA4 which was synthesized from RNA3 in infected cells. Therefore, preparation of BMV-IFN chimera RNA4 having IFN translation efficiency in the protein translation system in vitro was attempted, by replacing the CP2 gene in RNA 4 with the IFN gene.

The plasmid pBB3 has BMV full length cDNA3, and its cDNA is cut off from the plasmid as a SnaI-ECoRI fragment. The plasmid pUCT7 has a T7 promoter sequence and NsiI site. After annealing the oligonucleotide 5'pd(GTATTTAATG) (Seq. ID. No.: 12) and 5'pd(TCGACATTAAATAC) (Seq. ID. No.: 13), thus obtained fragment was introduced into SnaBI-EcoRI site in pBB3 to construct pBB4. pBB4 has a SnaBI cleavage site at the coincide site with the 5' end of BMVcDNA4. After cleavage of pUCT7 with NsiI, it was blunt ended using a T4DNA polymerase treatment and EcoRI cleavage was performed. Furthermore, the thus obtained DNA was ligated with the SnaBI-EcoRI fragment of pBB4 (BMVcDNA insert) to construct pBTF4. The pBTF4 was cleaved with SnaI and EcoRI, the thus obtained large fragment was ligated with the small fragment which was obtained by cleaving pBTFCP2IFN with SalI and EcoRI to construct pBTFsCP2IFN. From these plasmids, RNA was transcribed in vitro by the method of Example 1B-2, to obtain the wild type BMVRNA4 and FsCP2IFN which is BMV-IFN chimera RNA4 and in which CP2 were replaced with the IFN gene.

F. Analysis of the Protein Translated In Vitro From BMV-IFN Chimera RNA 4 in Which CP2 was Replaced By IFN Gene.

Wild type BMVRNA4 and FsCP2IFN were added to a wheat germ extracts in vitro protein translation system (Amersham Co.), and the protein was translated in vitro. After electrophoresis using SDS polyacrylamide gel, the translated products were compared and analyzed. As a result, the amounts of IFN translated from the second ATG was about 50 times that of IFN translated from the first ATG. On the otherhand, in wild type RNA4, substantively almost the same amounts of CP1 and CP2 were translated. From the above results, when CP2 was replaced with an exogenous gene, it can be seen that the translation of protein started from the second translation initiation codon, i.e., translation initiation codon of the exogenous gene and genuine exogenous gene product, and not fusion protein with the coat protein, was translated in high efficiency.

G. Replication of BMV-IFN Chimera RNA in Plant Cell Which Produces BMV Replicase Protoplasts were prepared from the BMRP(1+2) plant prepared in C-6 in which la and 2a proteins that are BMV replicase were prepared but BMV RNA1 and 2 were not replicated by replicase because 3' end of BMV RNA1 and 2 produced from the genome is deleted. The protoplast obtained was inoculated with each BMV-IFN chimera RNA and wild type BMVRNA3 as a control after mixing such with RNA1+2 respectively. Then, the entire RNA was prepared, Northern blotting was conducted using the 3' end sequence as a probe which is common to the entire BMVRNA, and replication of the chimera RNA and synthesis of subgenomic RNA in each experimental zone were compared with wild type BMVRNA3.

| | Replication of Chimera RNA | Synthesis of Subgenomic RNA |
|---|---|---|
| F1aIFN | 1 | — |
| F2aIFN | 1 | — |
| F3a1IFN | 1 | — |
| F3a4IFN | 20 | 80 |
| F3a5IFN | 10 | 40 |
| FCP1IFN | 50 | 20 |
| FCP2IFN | 50 | 20 |
| RNA3 | 100 | 100 |

As a result, F1aIFN, F2AIFN and F3a1IFN replicated little, but F3a4IFN, F3a5IFN, FCP1IFN and FCP2IFN were replicated with relatively high efficiency, although replication was inferior to the case where the wild strain RNA3 was used and the result was almost the same as in Example 3C. Thus, this demonstrated that all results obtained in Example 3A–F were effective also where a transformed plant was used.

EXAMPLE 4

Production of GUS

BMV ATCC66 as a RNA plant virus and β-glucuronidase gene (GUS) as a desired exogenous gene were used. The GUS gene was frequently used as a reporter gene because sensitivity of measuring of enzyme activity is high. Further the size of the gene is about three times as large as the BMV coat protein gene.

A. Construction of BMV-GUS Chimera RNA Transcription Vector, RNA Transcription In Vitro and Inoculation of Tobacco Protoplast By the same method as in the case of the construction of BMV-IFN chimera RNA transcription vector, 1a, 2a, 3a, CP1 and CP2 genes were replaced with GUS genes. NsiI and SacI sites were incorporated into the initiation and end codon in GUS gene using oligonucleotide 5'pd(GTGGTCAGTCATGCATGTTACGTA) (Seq. ID. No.: 14 ) and 5'pd(AATGAATCAAGAGCTCTCCTGGCG) (Seq. ID. No.: 15 ) to construct pUCGUS(Nsi).

The plasmids pBTF1aGUS, pBTF2aGUS, pBTF3a1-GUS, pBTF3a4GUS, pBTF3a5GUS, pBTFCP1IFN and pBTFCP2IFN were constructed using pUCGUS(-

Nsi) in place of pUCGUS(Nsi) using the same method as in the case of the construction of BMV-GUS chimera RNA transcription vector described in Example 3A.

From the plasmid thus obtained, RNA was transcribed using the method of Example 1B-2 and 7 kinds of RNA were thus obtained and designated F1aGUS, F2aGUS, F3a1GUS, F3a4GUS, F3a5GUS, FCP1IFN and FCP2IFN (FIG. 16).

A tobacco protoplast was inoculated with each BMV-GUS chimera RNA and wild type BMVRNA3 as a control by the method of Example 2C after mixing such with RNA1+2, respectively.

B. Replication of BMV-GUS Chimera RNA

Entire RNA was prepared from tobacco protoplast inoculated with BMV-GUS chimera RNA mixed with RNA1 and 2, respectively, and the Northern blotting was performed using the 3' end sequence which is common to the entire BMVRNA. Replication of chimera RNA and synthesis of subgenomic RNA were compared. However, the replication of chimera RNA was at an extremely low level compared with the replication of the wild type BMVRNA, therefore it was impossible to compare such with the wild type BMVRNA. Thus, Northern blotting was performed using a probe specific to the GUS gene. The results obtained were as follows when the average value of the RNA in the experimental zone using FCP2GUS in which the highest replication of chimera RNA observed and synthesis of subgenomic RNA was made 100%.

|  | Replication of Chimera RNA | Synthesis of Subgenomic RNA |
| --- | --- | --- |
| F1aGUS | 0 | — |
| F2aGUS | 0 | — |
| F3a1GUS | 0 | — |
| F3a4GUS | 100 | — |
| F3a5GUS | 50 | — |
| FCP1GUS | 100 | — |
| FCP2GUS | 100 | 100 |

As a result, only F3a4GUS, F3a5GUS, FCP1GUS and FCP2GUS were replicated, and in FCP1GUS and FCP2GUS, subgenomic RNA were also detected.

C. Analysis of Production Amounts of GUS and GUS Activity in Protoplast With Which BMV-GUS Chimera RNA was Inoculated Each BMV-GUS chimera RNA described above was mixed with RNA1 and 2 respectively, and a tobacco protoplast was inoculated herewith. Forty-eight hours after inoculation, whole protein was extracted from the tobacco protoplast, production amounts of GUS in each experimental zone were measured by the Western blotting analysis using anti-GUS antibody. Further, by using the following method, the GUS activity was measured. At first according to the method of Jefferson et al. (Jefferson et al., EMBO J. (1987), 6:3901–3907), protoplast extracts were prepared. The GUS activity level was detected by comparing enzymatic conversion of 4-methyl unberyferyl grucronilide as a substrate for 4-methyl unberyferron based on long wave ultraviolet light with GUS activity as a standard. The results were as follow, when the average value of the IFN production amounts and GUS activity in the experimental zone where FCP2IFN was used and the highest IFN production amounts and GUS activity exhibited set at 100%.

|  | Amount of GUS Production | GUS Activity |
| --- | --- | --- |
| F1aGUS | 0 | 3 |
| F2aGUS | 0 | 3 |
| F3a1GUS | 0 | 3 |
| F3a4GUS | 20 | 30 |
| F3a5GUS | 10 | 15 |
| FCP1GUS | 0 | 3 |
| FCP2GUS | 100 | 100 |

As a result of Western blotting, GUS was determined to be produced only in the experimental zone using F3a4GUS, F3a5GUS and FCP2GUS. Out of these, the highest level of GUS production could be seen in the zone using FCP2GUS. But in the zone using FCP1GUS, GUS could not be detected using Western blotting. From the above results, it was determined that protein having relatively large molecular weight, such as GUS, was produced.

Thus, as a result of measuring GUS activity in each experimental zone, it has been shown that GUS was produced about 30 times in the experimental zone in which FCP2GUS was used, in comparison with the experimental zone in which FCP1 was used, despite the fact that the amount of subgenomic RNA synthesis was the same level as compared with that when FCP1GUS (Example 4B) was used.

From the above results, it can be seen that when a relatively large molecular weight protein, such as GUS is produced, improvement in the protein production efficiency is achieved by replacement of the CP2 gene and not the CP1 gene

EXAMPLE 5

Preparation of Tobacco Plant Which Produces All of BMV Genome RNA

A. Preparation of Tobacco Plant Which Produces BMV RNA3

Plant transformation vector pBICBR3 (FIG. 6) was introduced into A. tumefaciens by the method of Example 2A, tobacco was transformed with A. tumefaciens (pBICBR3) and transformants were selected by the method of Example 2B. The expression of BMV RNA3 transcribed from BMV RNA3 cDNA introduced into the plant genome was verified by the inoculation of the protoplast prepared from transformants with BMV RNA1+2, and Western blotting analysis using anti-BMV antibody as described in Example 2C. In the transformants in which the expression of BMV RNA3 was verified, subgenomic RNA4 is synthesized by the BMV replicase using RNA3 transcribed from plant genome as template, and coat protein is translated from the subgenomic RNA4. The pure diploid was obtained by the method Example 2C-6 from transformants in which the expression of BMV RNA3 was verified, and were designated as BRP3.

B. Introduction of BMV RNA3 cDNA into the Genome of Tobacco Plant Which Produces BMV Replicase In order to introduce BMV RNA3 cDNA into the genome of BRP(1+2) plant and BMRP(1+2) plant prepared in Example 2C-6, crossing between BRP(1+2) plant and BRP3 plant, and also between BMRP(1+2) plant and BRP3 plant were performed, respectively. The F1 plants derived from the crossing were designated as BRP(1+2+3) plant and BMRP(1+2+3) plant, respectively. Both plants were grown and the expression of coat protein were compared by the Western blotting analysis using anti-BMV antibody as described in Example 2C-3. The results obtained were as follows when the expression of the coat protein in the BMR(1+2+3) plant was set at 100%.

| | Average Value for Expression of Coat Protein |
|---|---|
| BRP(1 + 2) plant | 0 |
| BRP(1 + 2 + 3) plant | 100 |
| BMRP(1 + 2) plant | 0 |
| BMRP(1 + 2 + 3) plant | 130 |

Accordingly, it was confirmed that, in the case of BRP(1+2+3) plant and BMRP(1+2+3) plant, virus multiplication cycle through production of BMV replicase, synthesis of subgenomic RNA by the replicase and production of coat protein is proceeded by the virus RNA transcribed from plant genome without adding BMV RNA exogenously.

EXAMPLE 6

Expression of the IFN Gene Introduced into the Genome of Tobacco Plant Which Produces BMV Replicase A. Construction of a Plant Transformation Vector pBICIFN in Which BMV-IFN Chimera RNA3 cDNA Was Inserted (FIG. 18)

Vector pBICIFN was constructed to introduce into a plant genome BMV-IFN chimera RNA3 cDNA in which CP2 gene was replaced with IFN gene. XbaI/EcoRI fragment containing IFN gene of pBTFCP2IFN (FIG. 15) was introduced into plant transformation vector pBICBR3 (FIG. 6) at the XbaI/EcoRI site to construct pBICIFN.

B. Preparation of Tobacco Plant Which Produces BMV-IFN Chimera RNA3

Plant transformation vector pBICIFN was introduced into *A. tumefaciens* by the method of Example 2A, tobacco was transformed with *A. tumefaciens* (pBICIFN) and transformants were selected by the method of Example 2B. The Expression of BMV-IFN chimera RNA3 transcribed from BMV-IFN chimera RNA3 cDNA introduced into plant genome was verified by the inoculation with BMV RNA 1+2 of the protoplast prepared from transformants, and Western blotting analysis using anti-IFN antibody as described in Example 2C. In the transformants in which the expression of BMV-IFN chimera RNA3 was verified, chimera subgenomic RNA3 transcribed from plant genome as template, and coat protein is translated from the subgenomic RNA4. The pure diploid was obtained by the method of Example 2C-6 from transformants in which the expression of BMV-IFN chimera RNA3 was verified, and was designated as BRP3IFN.

C. Introduction of BMV-IFN Chimera RNA3 cDNA into the Genome of Tobacco Plant Which Produces BMV Replicase In order to introduce BMV-IFN chimera RNA3 cDNA into the genome of BRP(1+2) plant and BMRP(1+2) plant prepared in Example 2C-6, crossing between BRP(1+2) plant and BRP3IFN plant, and also between BMRP(1+2) plant and BRP3IFN plant were performed, respectively. The F1 plants derived from the crossing were designated as BRP(1+2+3IFN) plant and BMRP(1+2+3IFN) plant, respectively. Both plants were grown and the expression of IFN were compared by the Western blotting analysis using anti-IFN antibody as described in Example 2C-3. The results obtained were as follows when the expression of the coat protein in the BMR(1+2+3IFN) plant was set at 100%.

| | Average Value for Expression of Coat Protein |
|---|---|
| BRP(1 + 2) plant | 0 |
| BRP(1 + 2 + 3IFN) plant | 100 |
| BMRP(1 + 2) plant | 0 |
| BMRP(1 + 2 + 3IFN) plant | 120 |

In order to verify that IFN expression in BRP(1+2+3IFN) plant and BMRP(1+2+3IFN) plant was exhibited by the translation from BMV-IFN chimera RNA4 synthesized from chimera RNA3 as subgenomic RNA. Northern plot analysis was carried out using BRP(1+2+3IFN) plant and BMRP(1+2+3IFN) plant. The total RNA (20 ug) from each tobacco leaves was separated by agarose gel electrophoresis, transferred to a nylon membrane and analyzed using NsiI/SacI fragment of pUCIFN(NsiI) containing IFN gene as a probe. The bands corresponding to the chimera RNA3 and chimera RNA4 were detected. The results obtained were as follows when the expression of the coat protein in the BRP(1+2+3IFN) plant was set at 100%.

| | Replication of Chimera RNA3 | Synthesis of Chimera RNA4 |
|---|---|---|
| BRP(1 + 2) plant | 0 | 0 |
| BRP(1 + 2 + 3IFN) plant | 100 | 100 |
| BMRP(1 + 2) plant | 0 | 0 |
| BMRP(1 + 2 + 3IFN) plant | 120 | 130 |

Accordingly, it was confirmed that, in the case of BRP(1+2+3IFN) plant and BMRP(1+2+3IFN) plant, the production cycle of the desired gene products through production of BMV replicase, synthesis of subgenomic RNA by the replicase, and the translation of the subgenomic RNA is proceeded by the viral and chimera RNA transcribed from plant genome without adding them exogenously.

The present invention may be embodied in other specific forms without departing from the spirit or essential characteristics thereof. The present is therefore to be considered in all respects as illustrative and not restrictive, the scope of the invention being indicated by the appended claims rather than by the foregoing description and all changes which come within the meaning and range of equivalency of the claims are therefor intended to be embraced therein.

TABLE 1

| AB Medium | | |
|---|---|---|
| Solution 1 | $K_2HPO_4$ | 12 g |
| | $NaH_2PO_4$ | 4 g |
| Solution 2 | $NH_4Cl$ | 4 g |
| | $MgSO_4.7H_2O$ | 1.2 g |
| | KCl | 0.6 g |
| | $CaCl_2$ | 0.6 g |
| | $FeSO_4.7H_2O$ | 10 mg |
| Solution 3 | Glucose | 20 g |

TABLE 2

| LS Medium<br>Preparation Method for LS Medium (per 200 ml) | | |
|---|---|---|
| Stock 1 | $K_2HPO_4$ | 12 g |
| | $NaH_2PO_4$ | 4 g |
| Stock 2 | $NH_4Cl$ | 4 g |
| | $MgSO_4.7H_2O$ | 1.2 g |
| | KCl | 0.6 g |
| Stock 3 | $CaCl_2H_2O$ | 8.8 g |
| Stock 4 | $Na_2$-EDTA | 0.666 g |
| Stock 5 | $H_2BO_3$ | 0.124 g |
| | $MnSO_4.4H_2O$ | 0.172 g |
| Stock 5 | $ZnSO_4.4H_2O$ | 0.446 g |
| | KI | 0.017 g |
| | $Na_2MoO_4.2H_2O$ | 0.005 g |
| Stock 5' | $CuSO_4.5H_2O$ | 0.05 g |
| | $CoCl_2.6H_2O$ | 0.005 g |
| Stock 6 | Thiamine-HCl | 0.008 g |
| | Myo-inositol | 2.0 g |
| Stock 7 | Naphthalene acetate | 0.042 g |
| Stock 8 | 6-Benzyladenina (BAP) | 0.004 g |
| Stock 9 | 6-Benzyladenina (BAP) | 0.1 g |
| Stock 10 | Myo-Inositol | 2.0 g |
| | Glycine | 0.04 g |
| | Pridoxin-HCl | 0.01 g |
| | Nicotinic acid | 0.01 g |
| | Thiamine-HCl | 0.02 g |

BAP first is dissolved in 0.1N HCl 30 ml (sterilized in water), then add water to make 200 ml.

Preparation method for LS medium (1 l)

1) add 2 ml of Stock 5' to 200 ml of new Stock 5, and use the resultant solution thereafter.

2) add each of 10 ml of Stocks 1, 2, 3, 4, 5 and 6, respectively.

3) add Hormone Stock according to the following table.

4) add 30 g of sucrose to make 1 ml using ion exchange water.

5) adjust pH to 5.8–6.2 using NaOH or KOH.

6) add 0.8–1% of agar, and autoclave-sterilize using a pot incubator.

7) after cooling the pot to 50°–60° C., shake and mix it gently, and allow to stand at room temperature to solidify. Where antibiotic is added, after cooling pot to 50°–60° C., filter-sterilized antibiotic is added.

| Hormone Concentration (in case of tobacco) (per 1 L) | Stock 7 | Stock 8 | Stock 9 |
|---|---|---|---|
| For Callus (LS1) | 10 ml | 10 ml | — |
| For Germination (LS4) | 0.5 ml | — | 10 ml |
| For Rooting (LS7) | 2.5 ml | 5 ml | — |
| For Young Plant (LS8) | — | — | — |

What is claimed is:

1. A process for production of an exogenous gene or the expression product of the exogenous gene in a plant cell, which process comprises:

inserting into a plant genome;

(a) a cDNA of replicase gene from a multipartite (+) strand RNA plant virus, wherein the virus is brome mosaic virus, and (b) cDNA of a recombinant brome mosaic virus genomic RNA in which nucleotides beginning with an ATG codon, or a part thereof, subsequent from a first ATG codon counted from the 5'-end in cDNA of virus coat protein gene are replaced with a desired exogenous gene; or inoculating a plant cell including cDNA of replicase gene of a plant virus, wherein the virus is brome mosaic virus, with RNA synthesized from the cDNA of recombinant brome mosaic virus genomic RNA.

2. A process according to claim 1, wherein the nucleotides around the first ATG codon are genetically engineered to inhibit translation through the deletion or replacement of a nucleotide corresponding to the 5'-end non-translated region of the cDNA of virus coat protein gene; and nucleotides around a second ATG codon are genetically engineered so that translation begins from the second ATG codon.

* * * * *